(12) United States Patent
Kaku et al.

(10) Patent No.: US 12,071,043 B2
(45) Date of Patent: Aug. 27, 2024

(54) SENSOR UNIT, AND SEAT EQUIPPED WITH SENSOR UNIT

(71) Applicant: TS TECH CO., LTD., Saitama (JP)

(72) Inventors: Hiroyuki Kaku, Tochigi (JP);
Ryuichiro Hirose, Tochigi (JP);
Atsushi Kusano, Tochigi (JP);
Munetaka Kowa, Tochigi (JP)

(73) Assignee: TS TECH CO., LTD., Saitama (JP)

(*) Notice: Subject to any disclaimer, the term of this patent is extended or adjusted under 35 U.S.C. 154(b) by 386 days.

(21) Appl. No.: 17/296,269

(22) PCT Filed: Nov. 29, 2019

(86) PCT No.: PCT/JP2019/046696
§ 371 (c)(1),
(2) Date: May 24, 2021

(87) PCT Pub. No.: WO2020/111213
PCT Pub. Date: Jun. 4, 2020

(65) Prior Publication Data
US 2022/0024352 A1    Jan. 27, 2022

(30) Foreign Application Priority Data

Nov. 29, 2018  (JP) ................. 2018-223962
Nov. 30, 2018  (JP) ................. 2018-225627
Sep. 27, 2019  (JP) ................. 2019-177721

(51) Int. Cl.
*B60N 2/00*    (2006.01)
*A61B 5/00*    (2006.01)

(52) U.S. Cl.
CPC ........... *B60N 2/002* (2013.01); *A61B 5/6891* (2013.01); *A61B 5/6893* (2013.01);
(Continued)

(58) Field of Classification Search
CPC .... B60N 2/002; B60N 2/0033; B60N 2/0034; B60N 2/003; B60N 2/0035; B60N 2/0021; B60N 2/0022
See application file for complete search history.

(56) References Cited

U.S. PATENT DOCUMENTS

2004/0189947 A1    9/2004  Hattori et al.
2010/0290215 A1*  11/2010  Metcalf ................. A47B 21/00
                                                            362/127
(Continued)

FOREIGN PATENT DOCUMENTS

DE         19963146 A1    7/2001
DE    102007012133 A1 *  9/2008  ............. B60N 2/002
(Continued)

OTHER PUBLICATIONS

Japanese Office Action mailed on May 30, 2023 from the Japan patent Office (JPO) for the related Japanese Patent Application No. 2018-223962, with machine English translation.
(Continued)

*Primary Examiner* — Timothy J Brindley
(74) *Attorney, Agent, or Firm* — Michael Best & Friedrich LLP

(57) ABSTRACT

To provide a sensor unit that can be easily attached to and detached from a seat in which a seated occupant is seated, and a seat equipped with a sensor unit. A sensor unit includes a sensor module including a biological sensor that detects a biological signal of a seated occupant, and a wireless communication unit that is connected to the biological sensor to wirelessly transmit the detected biological signal to an outside; and a sensor holder that holds the sensor module. The sensor holder includes a seat attachment portion detachably attached to an attached portion that is provided in a
(Continued)

front surface of a seat cushion at a position at which the seated occupant is abuttable against the attached portion.

8 Claims, 30 Drawing Sheets

(52) U.S. Cl.
CPC ......... *B60N 2/0021* (2023.08); *B60N 2/0022* (2023.08); *B60N 2/0031* (2023.08); *B60N 2/0032* (2023.08); *B60N 2/0034* (2023.08)

(56) References Cited

U.S. PATENT DOCUMENTS

| | | | | |
|---|---|---|---|---|
| 2013/0192904 | A1* | 8/2013 | Sprecher | B60N 2/002 177/136 |
| 2013/0207478 | A1* | 8/2013 | Metcalf | H04B 5/79 307/104 |
| 2015/0283923 | A1 | 10/2015 | Kordel et al. | |
| 2016/0089083 | A1 | 3/2016 | Sutton | |
| 2016/0317047 | A1* | 11/2016 | Sugiyama | A61B 5/308 |
| 2018/0035813 | A1* | 2/2018 | Fukuda | G01D 5/145 |
| 2018/0147985 | A1 | 5/2018 | Brown et al. | |
| 2018/0191178 | A1* | 7/2018 | Byrne | H02J 50/10 |
| 2019/0232786 | A1 | 8/2019 | Sasaki et al. | |
| 2020/0039382 | A1* | 2/2020 | Ozawa | B60N 2/80 |
| 2022/0242240 | A1 | 8/2022 | Sasaki et al. | |

FOREIGN PATENT DOCUMENTS

| | | | | |
|---|---|---|---|---|
| JP | S55-000633 | U | | 1/1980 |
| JP | H01-245287 | A | | 9/1989 |
| JP | 2001070091 | A * | 3/2001 | ............. B60N 2/002 |
| JP | 2004-224235 | A | | 8/2004 |
| JP | 2004-299591 | A | | 10/2004 |
| JP | 2009-208594 | A | | 9/2009 |
| JP | 2012-205902 | A | | 10/2012 |
| JP | 2013-052108 | A | | 3/2013 |
| JP | 2015-123359 | A | | 7/2015 |
| JP | 2016-009100 | A | | 1/2016 |
| JP | 2017-065504 | A | | 4/2017 |
| JP | 2017-136984 | A | | 8/2017 |
| JP | 2018-526258 | A | | 9/2018 |
| JP | 2019-130971 | A | | 8/2019 |
| KR | 20230136847 | A * | 9/2023 | |
| WO | WO-9958023 | A1 * | 11/1999 | ............. B60N 2/002 |
| WO | 2013/032013 | A | | 3/2013 |
| WO | WO-2014192636 | A1 * | 12/2014 | ........... A61B 5/6891 |
| WO | 2016/108511 | A1 | | 7/2016 |
| WO | 2018/186387 | A1 | | 10/2018 |

OTHER PUBLICATIONS

Extended European Search Report dated Dec. 15, 2021, for the corresponding European Patent Application No. 19889709.2.
Chinese Office Action dated Sep. 27, 2023 from the China National Intellectual Property Administration (CNIPA) for the corresponding Chinese Patent Application No. 201980076947.1, with English machine translation.
International Search Report mailed on Feb. 10, 2020 for the corresponding PCT Application No. PCT/JP2019/046696, with English machine translation.
Japanese Office Action mailed on Dec. 20, 2022 from the Japan Patent Office (JPO) for the related Japanese Patent Application No. 2018-223962, with English machine translation.
Chinese Office Action dated May 17, 2024 from the China National Intellectual Property Administration (CNIPA) for the 1 corresponding Chinese patent application No. 201980076947.1, with English machine translation.

* cited by examiner

SENSOR UNIT, AND SEAT EQUIPPED WITH SENSOR UNIT

CROSS-REFERENCE TO RELATED APPLICATIONS

This application is entering into the national phase of PCT Application No. PCT/JP2019/046696, filed on Nov. 29, 2019. Further, this application claims the benefit of priority from Japanese Application Number 2018-223962, filed on Nov. 29, 2018, Japanese Application Number 2018-225627, filed on Nov. 30, 2018, and Japanese Application Number 2019-177721, filed on Sep. 27, 2019, the entire contents of which are incorporated herein by reference.

TECHNICAL FIELD

The present invention relates to a sensor unit and a seat equipped with a sensor unit, and particularly to a sensor unit attached to a seat in which a seated occupant is seated, and a seat equipped with a sensor unit.

BACKGROUND ART

In the related art, a vehicle seat has been known which includes a function of measuring biological information of a driver during driving a vehicle. For example, a seat has been known which includes a function of being able to measure the heartbeat of a driver using a biological sensor that detects the bioelectric potential of the driver, and to quickly notify the driver when an abnormal change occurs in heartbeat (specifically, refer to PATENT LITERATURE 1).

In addition, a seat has been known which includes a function of estimating a physical condition of a driver using a biological sensor that detects the seating posture of the driver, and controlling the seat movement of the seat according to the result of estimation to cause the driver to recover from a fatigued state (specifically, refer to PATENT LITERATURE 2).

It has been disclosed that in the vehicle seat described in PATENT LITERATURE 1, a plurality of capacitive coupling type sheet-shaped sensors are disposed between a cushion pad forming a seat back and a trim cover, and the heartbeat of a seated occupant is measured based on the bioelectrical signal of the seated occupant detected from the sheet-shaped sensors. In this case, the plurality of sheet-shaped sensors are affixed and fixed to the cushion pad with an adhesive or the like.

In addition, it has been disclosed that in a seat control device described in PATENT LITERATURE 2, a plurality of piezoelectric elements as body pressure distribution sensors are fixed inside each of a seat back and a seat cushion, and the pressure according to the seating posture of an occupant is converted into a voltage signal to detect the body pressure distribution of the occupant, and when the physical condition of the occupant is estimated to be a fatigued state, the seat is controlled to move to cause the occupant to recover from fatigue.

CITATION LIST

Patent Literature

PATENT LITERATURE 1: JP 2015-123359 A
PATENT LITERATURE 2: JP 2017-65504 A

SUMMARY OF INVENTION

Technical Problem

By the way, in the vehicle seat as in PATENT LITERATURES 1 and 2, since the biological sensor (sensor unit) is configured to be fixed to the cushion pad of the seat back (seat cushion) with an adhesive or the like, it is difficult to remove the biological sensor from the seat.

In such a case, it is not possible that the type of the sensor unit is replaced according to a demand of the seated occupant who is a user, to change an output function based on the biological information obtained from the biological sensor. Therefore, the seat is lack of versatility, which is a problem. In addition, the sensor unit cannot be replaced at a proper replacement time, which is a problem.

In addition thereto, it has been anticipated that when the user can easily remove the sensor unit from the vehicle seat and attach the sensor unit to a work chair or the like separate from the vehicle seat, the output function can be used in various situations according to the sensor unit.

In addition, in the vehicle seat equipped with a biological sensor as in PATENT LITERATURES 1 and 2, the biological sensor having a sheet shape is fixed to the cushion pad with an adhesive, a double-faced tape, or the like, but is not fixed to a skin material on a seated occupant side, so that the position of the biological sensor is shifted. Therefore, the biological signal of the seated occupant cannot be stably detected, which is a problem.

In addition, it has been required to devise ways to take into consideration the seating feeling of the seated occupant while achieving a simple assembly configuration in terms of attaching the biological sensor to the vehicle seat.

The present invention has been made in view of the above problems, and an object of the present invention is to provide a sensor unit that can be easily attached to and detached from an object against which a human is abuttable, particularly a seat in which a seated occupant is seated, and a seat equipped with a sensor unit.

In addition, another object of the present invention is to provide a sensor unit that can be attached not only to conveyance seats but also various seats such as work chairs, and a seat equipped with a sensor unit.

In addition, still another object of the present invention is to provide a sensor unit that can stably detect a biological signal of a seated occupant, and a seat equipped with a sensor unit.

In addition, further another object of the present invention is to provide a sensor unit that takes into consideration the seating feeling of a seated occupant while achieving a simple assembly configuration, and a seat equipped with a sensor unit.

Solution to Problem

The above problems are solved by a sensor unit according to the present invention which is attached to an object against which a human is abuttable, the sensor unit including: a biological sensor that detects a biological signal of the human; a communication unit that is connected to the biological sensor to transmit the detected biological signal to an outside; and a sensor holder that holds the biological sensor and the communication unit. The sensor holder includes an attachment portion detachably attached to an attached portion that is provided in the object at a position at which the human is abuttable against the attached portion.

With the above configuration, it is possible to realize the sensor unit that can be relatively easily attached to and detached from the object against which the human is abuttable.

In this case, the sensor unit may be attached to a seat in which a seated occupant is seated. The biological sensor may detect a biological signal of the seated occupant. The sensor holder may include a seat attachment portion as the attachment portion detachably attached to the attached portion that is provided in the seat at a position at which the seated occupant is abuttable against the attached portion.

With the above configuration, it is possible to realize the sensor unit which can be relatively easily attached to and detached from a seating seat, and it is possible to realize the sensor unit that can be attached not only to conveyance seats but also various seats such as work chairs.

In this case, the sensor unit may further include a wireless communication unit as the communication unit that wirelessly transmits the detected biological signal to the outside; and a battery unit that is connected to the biological sensor and the wireless communication unit to supply electric power.

With the above configuration, it is possible to realize the sensor unit that has a simple configuration without separately requiring an election control unit (ECU) or a power supply for a vehicle seat unlike the related art, and it is easier for the seated occupant who is a user to remove the sensor unit from the seat to carry the sensor unit.

In this case, the sensor holder may be formed in a bag shape, and hold the biological sensor and the communication unit inside a bag.

With the above configuration, since the biological sensor and the communication unit are not in direct contact with a skin material or a cushion pad of a seat cushion (seat back) that is a seat side component, it is possible to suppress the positional shift of the biological sensor (communication unit) with respect to the seat, it is possible to protect the biological sensor itself, and it is possible to more stably detect the biological signal of the seated occupant.

Incidentally, the seat side component may be a headrest, an armrest, an ottoman, or the like.

In this case, the sensor holder may have a shape corresponding to a cushion recessed portion provided as the attached portion in a front surface of a seat cushion that is a seating portion of the seat, and may be stored and attached inside the cushion recessed portion.

With the above configuration, even when the sensor unit is attached to the front surface of the seat cushion, unevenness can be suppressed from being generated in the front surface of the seat cushion. Therefore, it is possible to take into consideration the seating feeling of the seated occupant while achieving a simple assembly configuration.

In this case, the biological sensor may be disposed to be interposed between the sensor holder and the cushion recessed portion that is provided in the seat cushion.

With such a configuration, the biological sensor (sensor unit) can be more stably attached to the seat.

In this case, the sensor holder may hold a plurality of the biological sensors. The plurality of biological sensors may be disposed at intervals in a seat width direction and/or in a seat front to rear direction, and may be disposed to correspond to positions at which the seated occupant is abuttable against the plurality of biological sensors.

As described above, since the sensor holder holds the plurality of biological sensors, with a relatively simple configuration, the plurality of biological sensors can be collectively attached to the seat.

In this case, the sensor holder may include the seat attachment portion that is attachable to the attached portion, which is provided in the seat, with the attached portion interposed between portions of the seat attachment portion.

With the above configuration, the sensor unit can be attached to and detached from the seat with a simple configuration.

In this case, a positioning display portion which displays a holding position of the biological sensor to the outside may be formed in a front surface of the sensor holder.

With the above configuration, it is possible to recognize the attachment position of the biological sensor from outside the sensor holder, and the positioning of the biological sensor with respect to the seat is facilitated.

In addition, it is also possible to realize a seat equipped with a sensor unit including the above sensor unit; and a seat cushion formed by covering a cushion pad with a skin material, in which the sensor unit is detachably attached between the skin material and the cushion pad on the seat cushion.

Advantageous Effects of Invention

According to the present invention, it is possible to realize the sensor unit that can be easily attached to and detached from the object against which the human is abuttable, particularly the seating seat, and it is possible to realize the sensor unit that can be attached to various seats.

In addition, according to the present invention, it is easier for the seated occupant to remove the sensor unit from the seat to carry the sensor unit.

In addition, according to the present invention, it is possible to suppress the positional shift of the biological sensor with respect to the seat, it is possible to protect the biological sensor itself, and it is possible to more stably detect the biological signal of the seated occupant.

In addition, according to the present invention, it is possible to take into consideration the seating feeling of the seated occupant while achieving a simple assembly configuration.

In addition, according to the present invention, it is possible to more stably attach the biological sensor (sensor unit) to the seat, and with a simple configuration, it is possible to collectively attach the plurality of biological sensors to the seat.

In addition, according to the present invention, the positioning of the biological sensor with respect to the seat is facilitated.

DESCRIPTION OF EMBODIMENTS

Hereinbelow, embodiments according to the present invention will be described with reference to FIGS. 1 to 28.

The present embodiment of the invention relates to a seat equipped with a sensor unit in which a seated occupant is seated, the sensor unit including a biological sensor that detects a biological signal of the seated occupant, a wireless communication unit that is connected to the biological sensor to wirelessly transmit the detected biological signal to the outside, and a sensor holder that holds the biological sensor and the wireless communication unit. The sensor holder includes a seat attachment portion detachably attached to an attached portion that is provided in a front surface of a seat cushion at a position at which the seated occupant is abuttable against the attached portion.

Incidentally, a side on which the seated occupant is seated with respect to a seat back of the seat equipped with a sensor unit is a seat front side.

Figure 1:
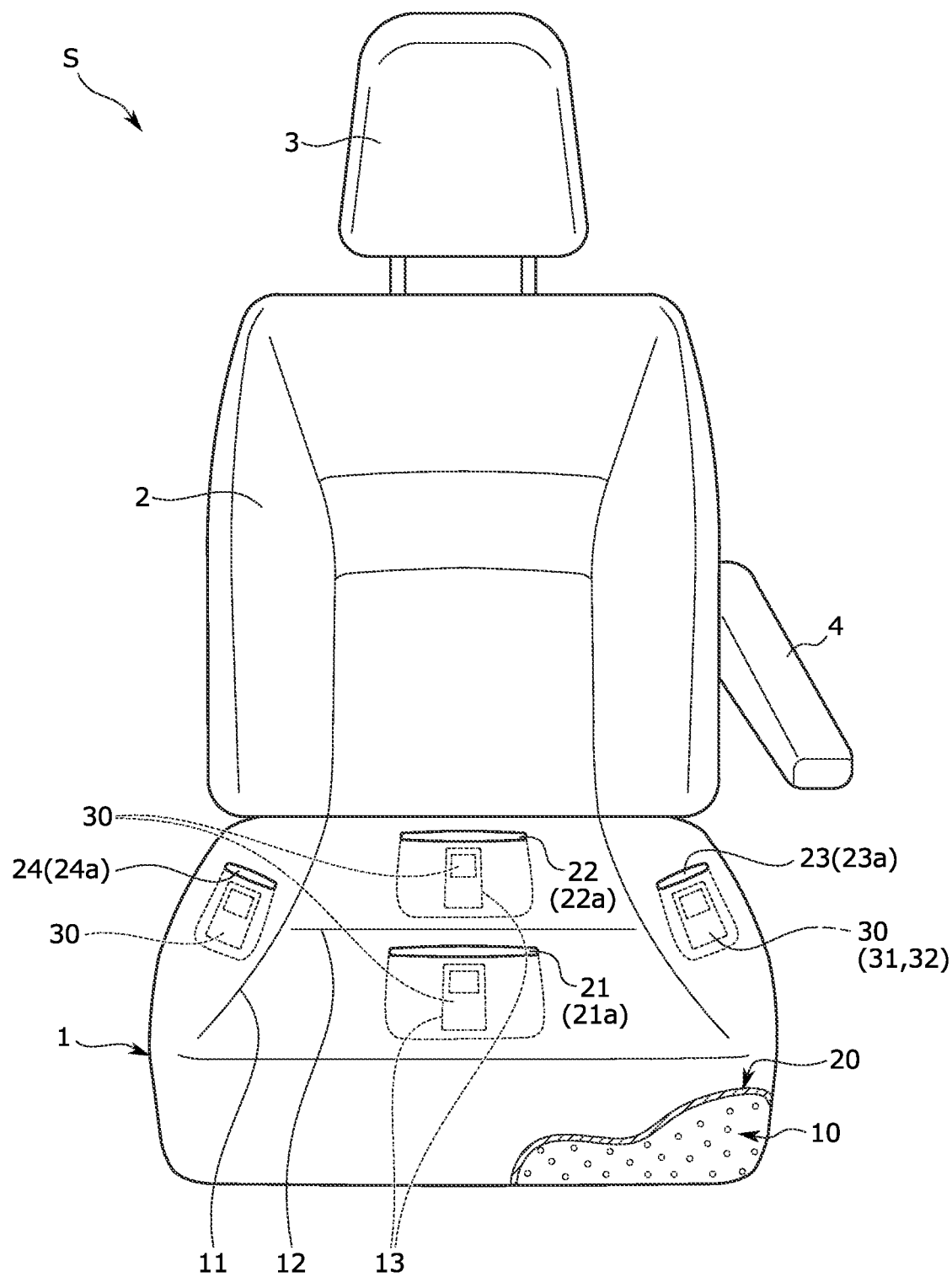
FIG. 1 is an external appearance perspective view of a seat equipped with a sensor unit of the present embodiment.

As illustrated in FIG. 1, a seat S equipped with a sensor unit in the present embodiment is a vehicle seat, and includes mainly a seat body including a seat cushion 1, a seat back 2, a headrest 3, and an armrest 4, and a sensor unit 30 that is attached inside the seat body (seat cushion 1), detects an electrical signal according to the bioelectric potential of a seated occupant seated in the seat, and transmits the detected electrical signal to the outside.

As illustrated in FIG. 1, the seat cushion 1 is a seating portion that supports the seated occupant from below, and is formed by placing a cushion pad 10 on a cushion frame that is not illustrated and is a skeleton, and covering the cushion pad 10 with a skin material 20.

The seat back 2 is a backrest portion that supports the back of the seated occupant from rear, and is formed by placing a cushion pad not illustrated on a back frame that is not illustrated and is a skeleton, and covering the cushion pad with a skin material not illustrated.

The headrest 3 is a head portion that supports the head of the seated occupant from rear, and is formed by placing a cushion pad not illustrated on a headrest pillar that is not illustrated and is a core, and covering the cushion pad with a skin material not illustrated.

The armrest 4 is an arm portion that supports the arm of the seated occupant from below, and is rotatably assembled to an outer surface in a seat width direction of the seat back 2 via an attachment bracket not illustrated.

The cushion pad 10 is a cushion material formed of foamed urethane or the like. As illustrated in FIG. 1, skin pull-in grooves 11 extending in a seat front to rear direction, and a skin pull-in groove 12 extending in the seat width direction to connect the skin pull-in grooves 11 on right and left sides are formed in right and left side portions in the seat width direction on a front surface of the cushion pad 10.

In addition, in order to secure seating feeling, a cushion recessed portion 13 corresponding to the outer shape of the sensor unit 30 is formed in a portion on the front surface of the cushion pad 10, the portion facing the sensor unit 30.

The skin material 20 is formed of a cloth material, a leather material, or the like having elasticity, and is formed, for example, by sewing a conductive thread as necessary to a base cloth made of a natural fiber or a synthetic fiber.

Incidentally, in order to improve seating feeling for the seat cushion 1, a wadding material not illustrated may be attached to a back surface of the skin material 20.

Skin pockets 21 and 22 each storing the sensor unit 30 thereinside are formed in a seat portion in front of the skin pull-in groove 12 and in a seat portion therebehind on a front surface of the skin material 20, respectively. In addition, skin pockets 23 and 24 are formed in portions outside the skin pull-in grooves 11 on the right and left sides in the seat width direction, respectively.

The skin pockets 21 to 24 are bag-shaped pocket portions formed by separately attaching a cloth material or the like to a back surface of a body portion of the skin material 20 by sewing, and can store the sensor units 30 through pocket openings 21a to 24a provided on the front surface of the skin material 20.

The skin pockets 21 and 22 on front and rear sides are disposed in a central portion in the seat width direction of the seat cushion 1, and are disposed side by side in the seat front to rear direction.

In addition, the skin pockets 23 and 24 on the right and left sides are disposed at positions facing each other in the seat front to rear direction.

Figure 2A:
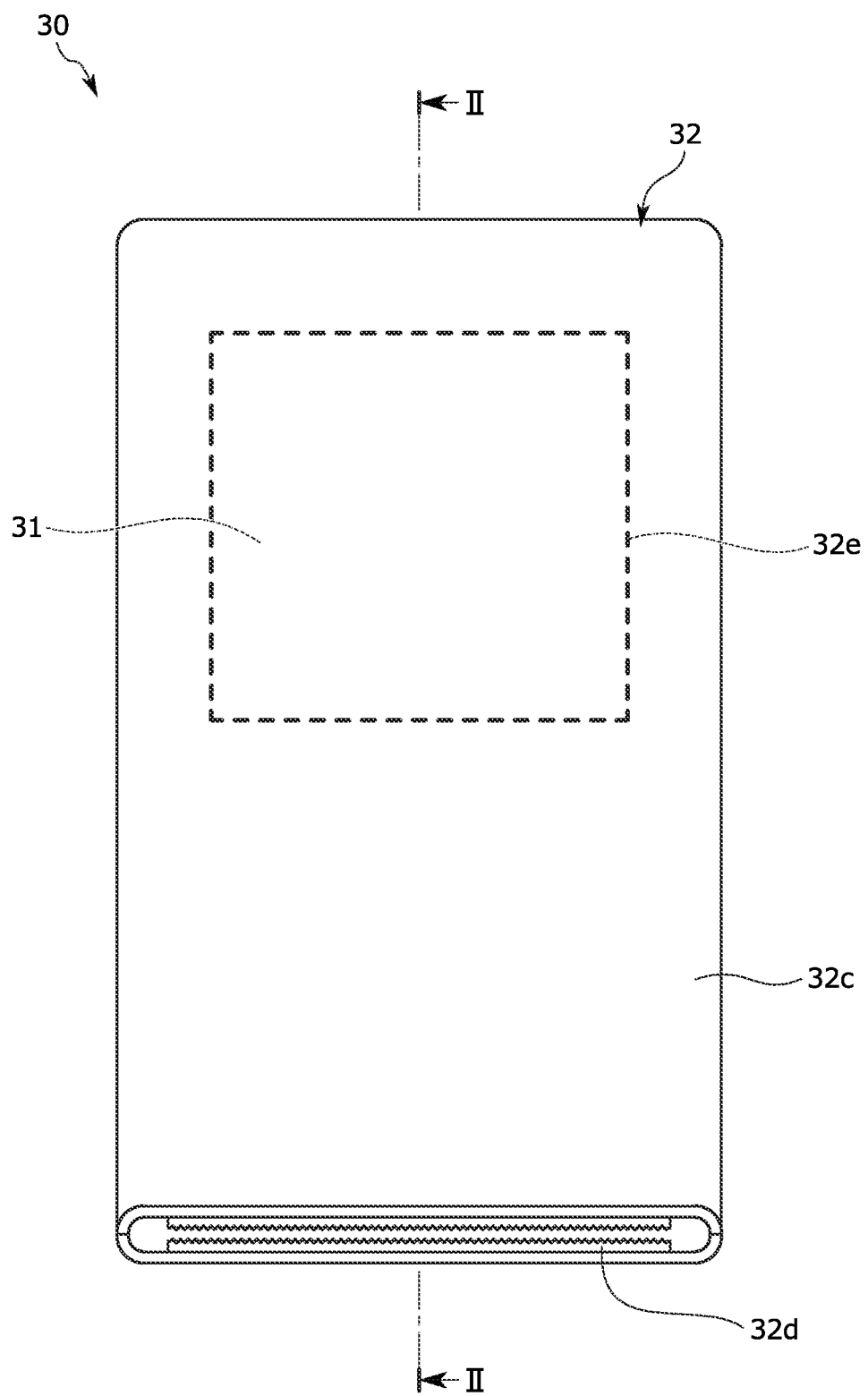
FIG. 2A is a front view of a sensor unit.
Figure 2B:
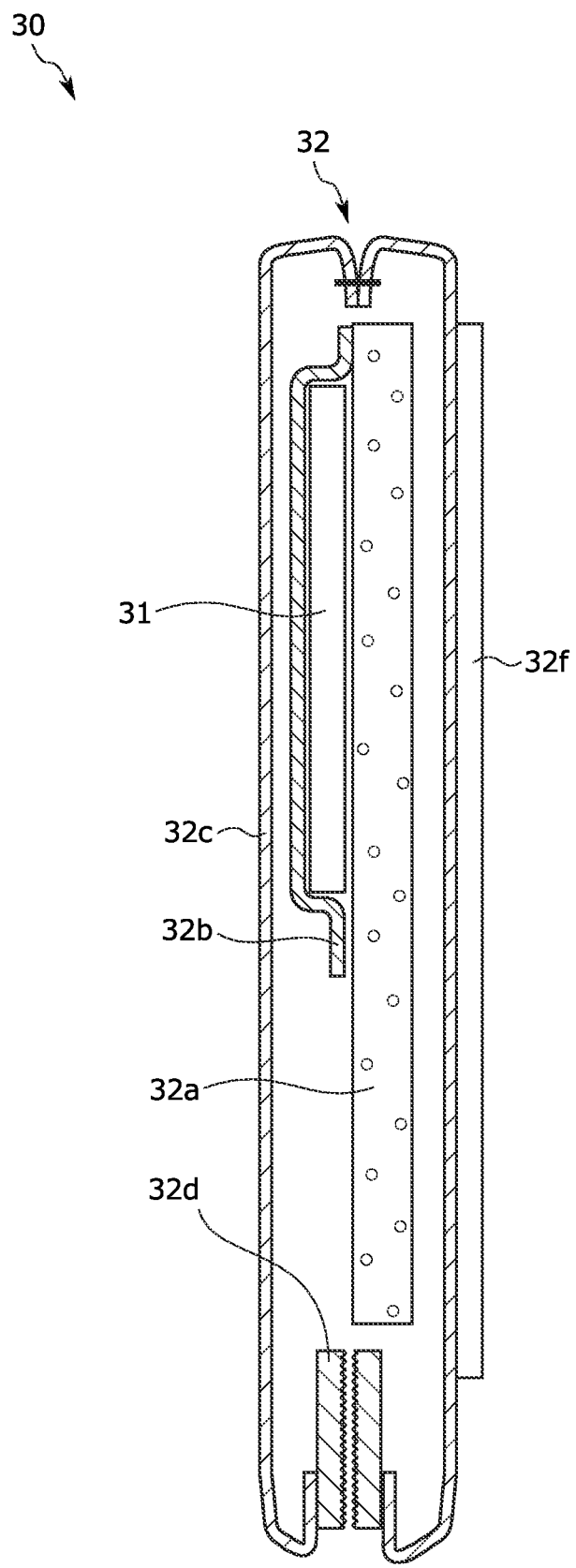
FIG. 2B is a cross-sectional view taken along line II-II in FIG. 2A, and is a view illustrating a configuration of the sensor unit.

As illustrated in FIGS. 2A and 2B, the sensor unit 30 includes mainly a sensor module 31 including a biological sensor 31a, and a sensor holder 32 that has a bag shape and holds the sensor module 31. The sensor units 30 are detachably attached to the skin pockets 21 to 24 (attached portions) provided in the seat cushion 1 at positions at which the seated occupant is abuttable against the skin pockets 21 to 24.

Figure 3:
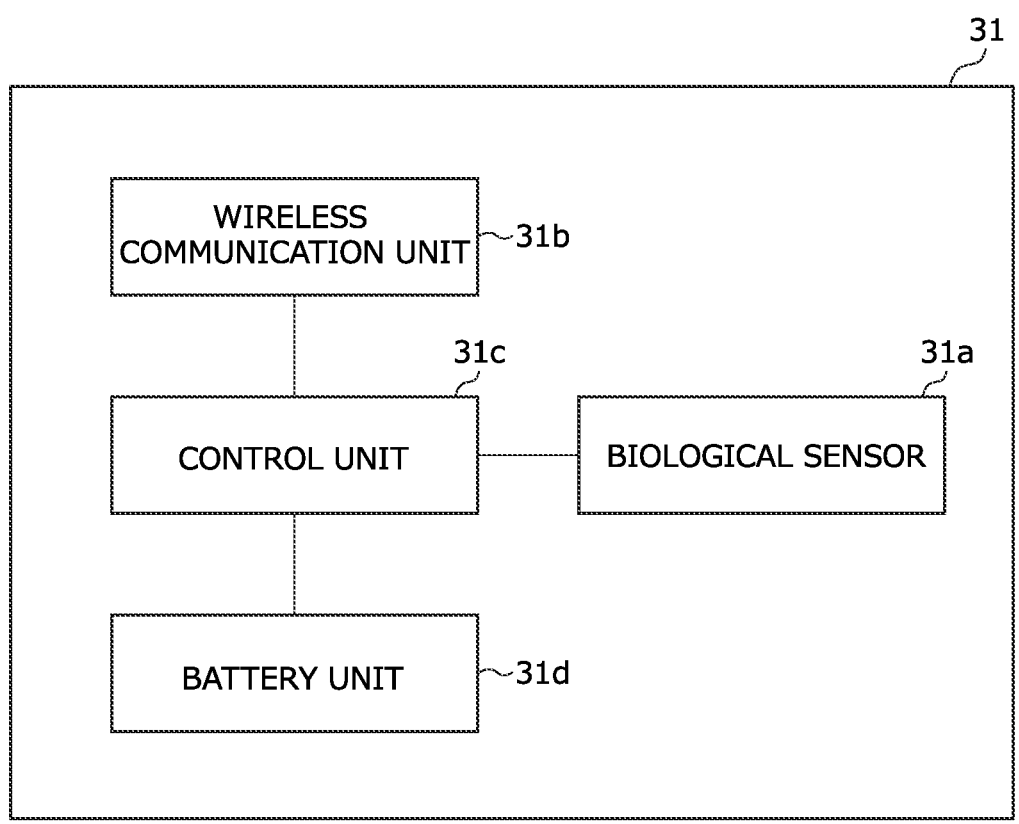
FIG. 3 is a diagram illustrating a hardware configuration of the sensor unit of a wireless type.

As illustrated in FIG. 3, the sensor module 31 includes mainly the biological sensor 31a that detects an electrical signal according to the bioelectric potential of the seated occupant; a wireless communication unit 31b that receives the electrical signal to wirelessly transmit the electrical signal to the outside; a control unit 31c that performs a process of transmitting the electrical signal, which is detected by the biological sensor 31a, to the wireless communication unit 31b; and a battery unit 31d that supplies electric power.

The biological sensor 31a is specifically a sensor that detects the respiratory signal (electrical signal) of the seated occupant, and more specifically a planar pressure sensor that detects the seating pressure of the seated occupant.

Incidentally, the "seating pressure" is a value that periodically changes according to the physiological activity (respiration) of the seated occupant when the seated occupant is seated in the seat S equipped with a sensor unit.

The wireless communication unit 31b is connected to an external terminal, for example, a computer such as a tablet terminal, a smartphone, or a PC or an electrical device using a wireless communication technique to transmit and receive an electrical signal (data signal).

The control unit 31c corresponds to a microcomputer, and comprehensively executes electrical control, and the battery unit 31d is a relatively small button battery.

As illustrated in FIGS. 2A and 2B, the sensor holder 32 is a substantially rectangular bag body, and includes mainly a cushion material 32a that has a substantially flat plate shape and supports the entirety of the sensor module 31 from below; a cloth member 32b that is attached to cover the entirety of the sensor module 31 from above; and a cover material 32c that has a bag shape and stores the sensor module 31, the cushion material 32a, and the cloth member 32b thereinside.

The cloth member 32b is, for example, a nonwoven tape, and all four end portions thereof abut against and are affixed to a front surface of the cushion material 32a. Incidentally, all the four end portions may be affixed with an adhesive or the like.

The cover material 32c is formed by superimposing a pair of skin covers on top of each other in a surface-to-surface manner, forming one end portion as an opening portion, and sewing the remaining end portion, and a pair of hook-and-loop fasteners are provided on an inner surface of the opening portion of the cover material 32c, as a cover closing portion 32d.

In addition, the internal space of the cover material 32c is formed with substantially the same size as that of the outer shape of the cushion material 32a, and the sensor module 31 is stored inside the cover material 32c without being shifted in position.

A positioning display portion 32e which displays the holding position of the sensor module 31 to the outside is formed in a front surface of the sensor holder 32, as a rectangular sewing line (stitch). Incidentally, instead of the sewing line, a separate cushion material (urethane slab) having a rectangular shape may be affixed.

In addition, a seat attachment portion 32f which can come into surface-to-surface contact with and be attached to each of the skin pockets 21 to 24 (attached portions) of the seat cushion 1 is provided on a back surface in an outer surface of the sensor holder 32, the back surface being on an opposite side from the front surface in which the positioning display portion 32e is formed.

The seat attachment portion 32f may be formed, for example, as a hook-and-loop fastener, or in addition thereto, may be formed as a double-faced tape to be attached to an inner surface of each of the skin pockets 21 to 24 with detachable adhesion. When hook-and-loop fasteners are adopted, the configuration may be such that one hook-and-loop fastener (for example, a hook side) as the seat attachment portion 32f can be attached to and detached from the other hook-and-loop fastener (for example, a loop side) provided on the inner surface of each of the skin pockets 21 to 24.

In the above configuration, the sensor unit 30 is connected to a known heartbeat measuring device not illustrated through a network, so that the heartbeat measuring device can measure the heartbeat of the seated occupant based on the respiratory signal (electrical signal) of the seated occupant transmitted from the sensor unit 30, to quickly notify the seated occupant when an abnormal change occurs in heartbeat.

Incidentally, regarding a specific method for calculating a heart rate based on the electrical signal from the sensor unit 30, a known calculation method (for example, a calculation method described in JP 2015-123359) can be used, and a specific description will be omitted.

In addition thereto, the type of the biological sensor can be changed according to a demand of the seated occupant who is a user, to change an output function based on biological information detected from the biological sensor.

Specifically, in addition to a pressure sensor, a temperature sensor, a sound sensor, an optical sensor, an odor sensor, an acceleration sensor, or the like may be adopted.

In addition, in addition to measuring a change in heartbeat of the seated occupant to notify the seated occupant of an abnormality (dozing state) in heartbeat, the output function is assumed to be measuring the seating posture of the seated occupant and controlling the seat movement of the seat to direct a relax mode or a skeleton correction mode to the seated occupant, directing a game or an image to the seated occupant based on the biological information (for example, electrocardiogram, blood pressure, body temperature, respiration, or the like) of the seated occupant.

Second Embodiment of Seat Equipped with Sensor Unit

Next, a seat S2 equipped with a sensor unit which is a second embodiment will be described with reference to FIG. 4.

In the seat S2 equipped with a sensor unit, the configuration of a sensor unit 130 differs mainly from that in the seat S equipped with a sensor unit.

The sensor unit 130 includes mainly a sensor module 131, and a sensor holder 132 that has a block shape and holds the sensor module 131, and is detachably attached to a cushion recessed portion 113 (attached portion) that has a rectangular parallelepiped shape and is formed on a front surface of a cushion pad 110 of a seat cushion 101.

The sensor module 131 has the same configuration as that of the sensor module 31 illustrated in FIG. 3.

The sensor holder 132 is a pad member formed of a rectangular parallelepiped block, and is formed in a shape corresponding to the cushion recessed portion 113. A storage recessed portion 133 which stores the sensor module 131 is formed on a front surface of the sensor holder 132.

In this case, the sensor holder 132 (outer surface of the sensor holder 132) corresponds to a "seat attachment portion", and is detachably attached to the cushion recessed portion 113 (attached portion).

Even in the above configuration, the sensor unit which can be relatively easily attached to and detached from a seating seat can be realized, and can be attached not only to conveyance seats but also various seats such as work chairs.

Third Embodiment of Seat Equipped with Sensor Unit

Figure 5:
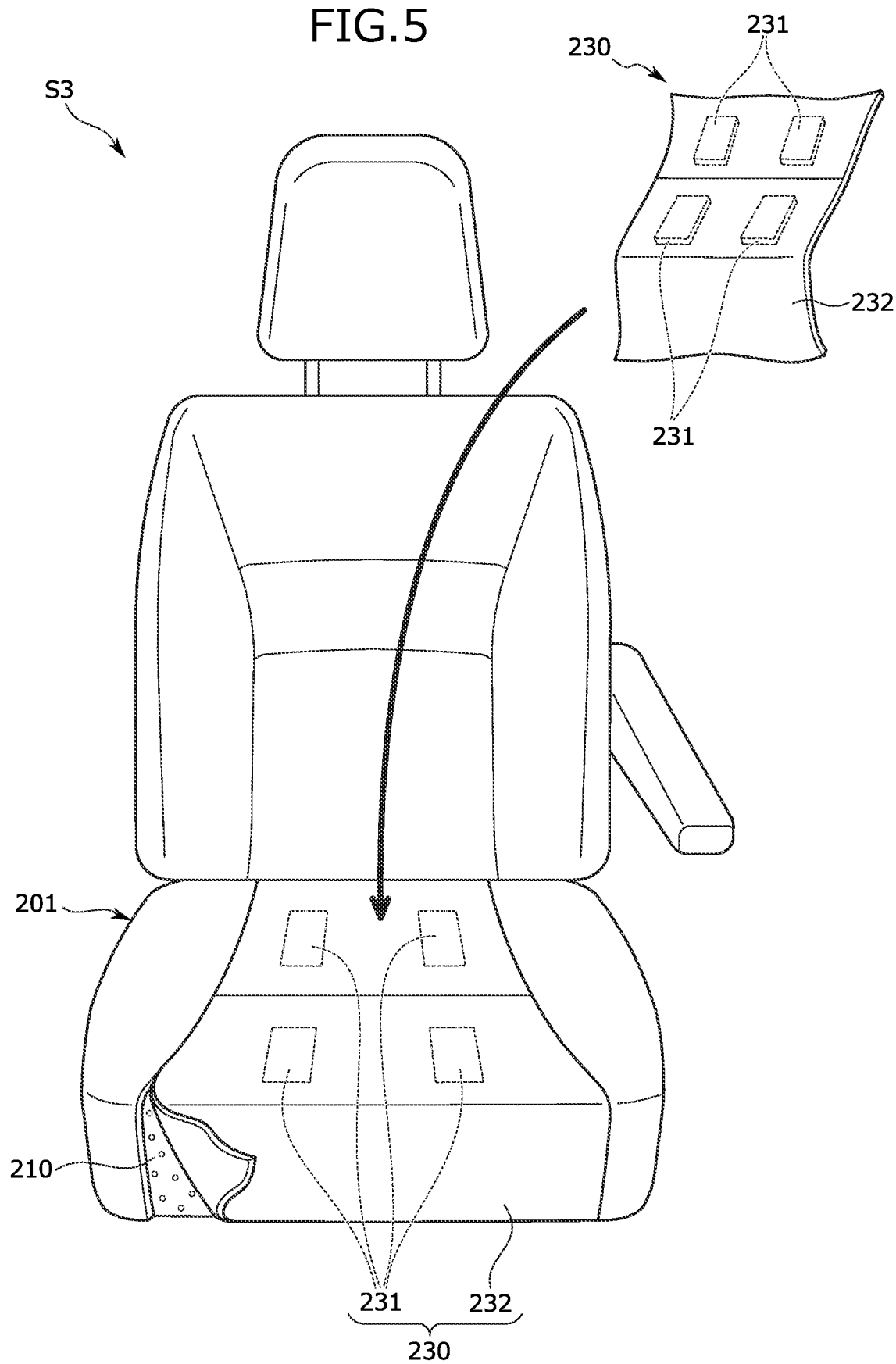
FIG. 5 is an external appearance perspective view of a seat equipped with a sensor unit in a third embodiment.

Next, a seat S3 equipped with a sensor unit which is a third embodiment will be described with reference to FIG. 5.

In the seat S3 equipped with a sensor unit, the configuration of a sensor unit 230 differs mainly from that in the seat S equipped with a sensor unit.

The sensor unit 230 includes mainly a plurality of sensor modules 231, and a sensor holder 232 that has a sheet shape and collectively holds the plurality of sensor modules 231, and is detachably hooked to a cushion pad 210 (attached portion) of a seat cushion 201.

The sensor module 231 has the same configuration as that of the sensor module 31 illustrated in FIG. 3. The plurality of sensor modules 231 are disposed at intervals in the seat width direction and in the seat front to rear direction in a total of four locations corresponding to positions at which the seated occupant is abuttable against the plurality of sensor modules 231.

The sensor holder 232 is a piece of skin material, and is formed on a front surface of a central portion of the cushion pad 210 in a shape in which the sensor holder 232 can cover the front surface.

The plurality of sensor modules 231 are attached to a back surface of the sensor holder 232 with a hook-and-loop fastener or a double-faced tape.

In this case, the sensor holder 232 corresponds to a "seat attachment portion", and is detachably hooked and attached to the cushion pad 210 (attached portion).

Even in the above configuration, the sensor unit which can be relatively easily attached to and detached from a seating seat can be realized, and can be attached not only to conveyance seats but also various seats such as work chairs.

In addition, with a relatively simple configuration, the plurality of biological sensors can be collectively attached to a seating seat.

Fourth Embodiment of Seat Equipped with Sensor Unit

Next, a seat S4 equipped with a sensor unit which is a fourth embodiment will be described with reference to FIGS. 6 and 7.

In the seat S4 equipped with a sensor unit, a sensor unit 330 is a wired communication type as compared with the seat S equipped with a sensor unit.

Figure 6:
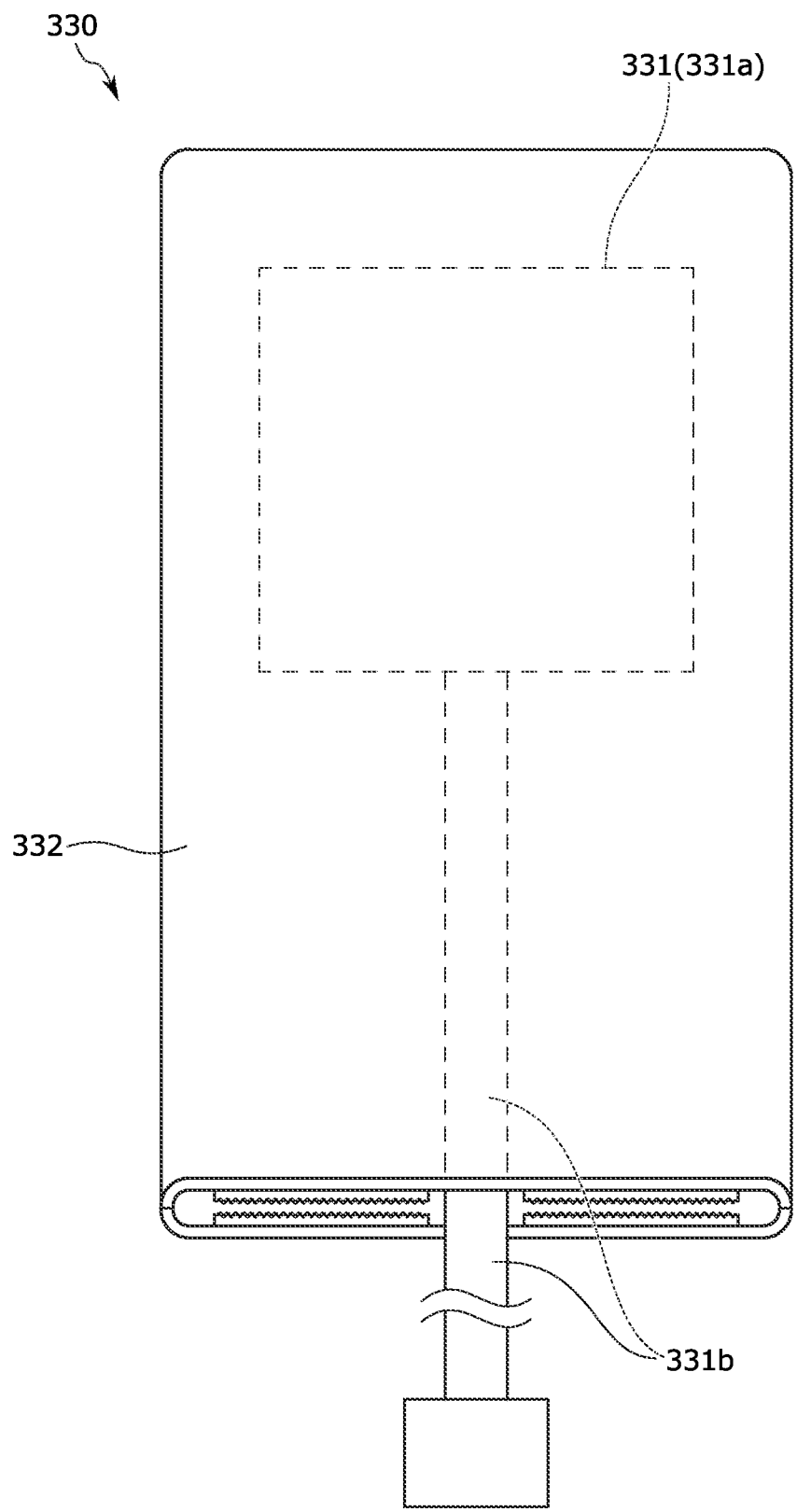
FIG. 6 is a view illustrating a hardware configuration of a sensor unit of a wired type in a seat equipped with a sensor unit in a fourth embodiment.

As illustrated in FIG. 6, in the sensor unit 330, a sensor module 331 includes a biological sensor 331a, and a wired communication unit 331b that is connected to the biological sensor 331a to transmit a detected biological signal to the outside.

Figure 7:
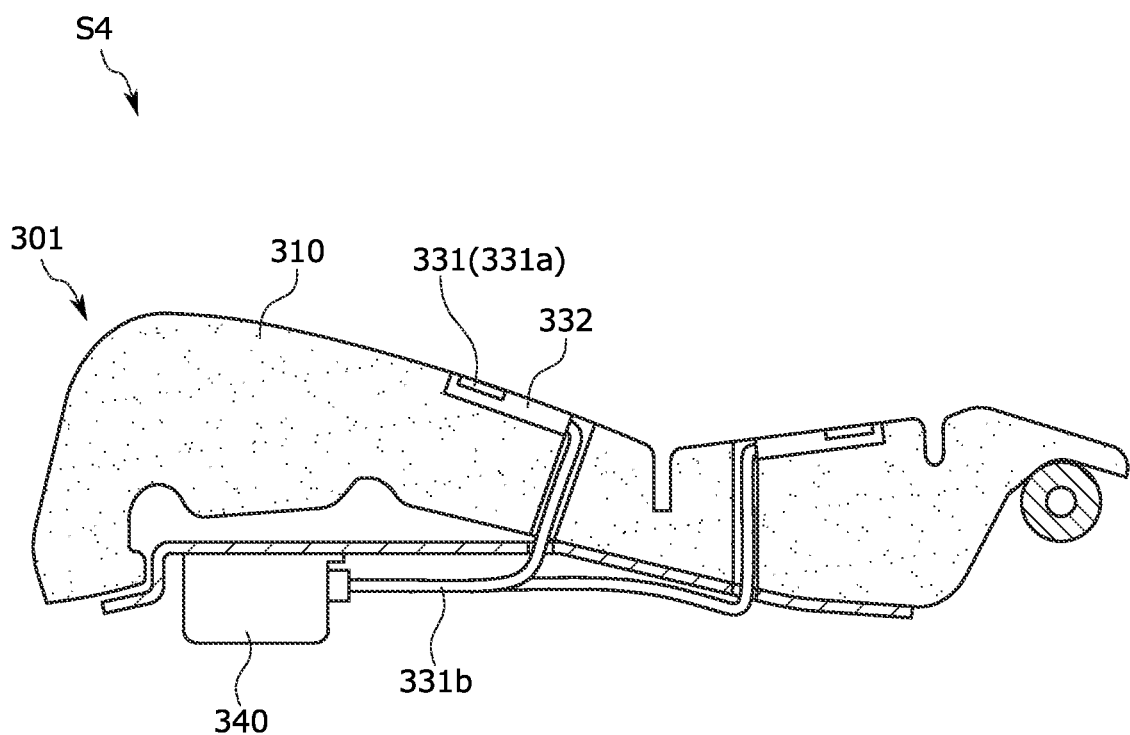
FIG. 7 is a view illustrating the disposition of the sensor unit of a wired type in FIG. 6 in the seat.

As illustrated in FIG. 7, the wired communication unit 331b includes conductive wires that connect the biological sensor 331a and an ECU 340 provided in a seat cushion 301, to output a biological signal, which is obtained from the biological sensor 331a, toward the ECU 340, and a harness that is a bundle of the conductive wires.

In detail, the wired communication unit 331b bends from a sensor holder 332 toward a seat lower side to extend and pass through a through-hole of a cushion pad 310, to bend toward a seat front side to extend along a bottom surface of a cushion frame, and then to be connected to the ECU 340.

The ECU 340 is a control part of a known heartbeat measuring device that can analyze the biological signal, which is detected by the sensor unit 330, to calculate the heart rate of the seated occupant, and is attached to the bottom surface of the cushion frame. Incidentally, a power supply battery not illustrated is provided in a peripheral portion of the ECU 340.

Even in the above configuration, the sensor unit which can be attached to and detached from a seating seat can be realized, and is a sensor unit that is replaceable in various conveyance seats.

Fifth Embodiment of Seat Equipped with Sensor Unit

Next, a seat S5 equipped with a sensor unit in a fifth embodiment will be described with reference to FIG. 8 to FIGS. 10A and 10B.

A sensor unit 430 of the seat S5 equipped with a sensor unit is a wired communication type.

Figure 8:
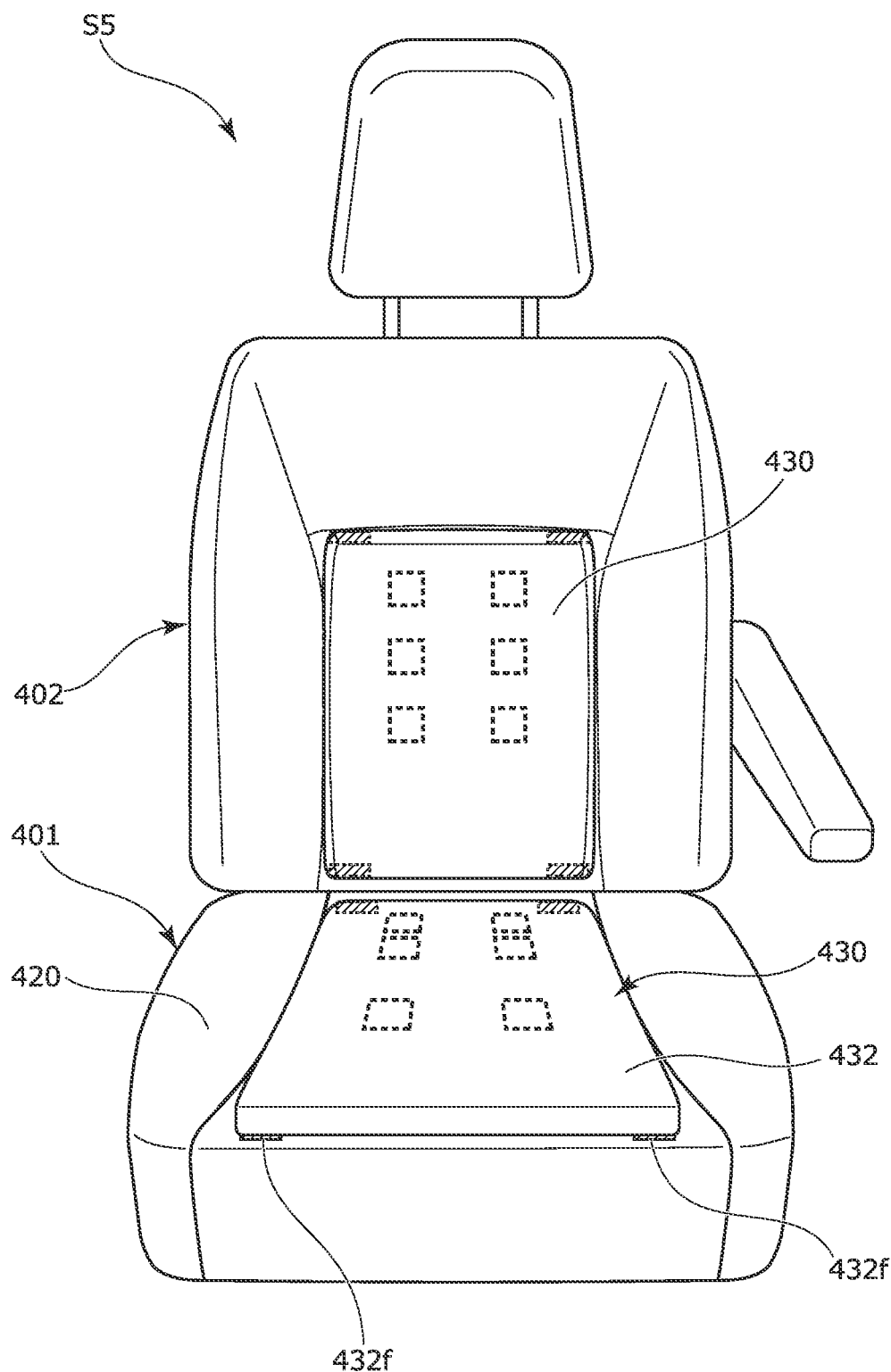
FIG. 8 is an external appearance perspective view of a seat equipped with a sensor unit in a fifth embodiment.
Figure 9:
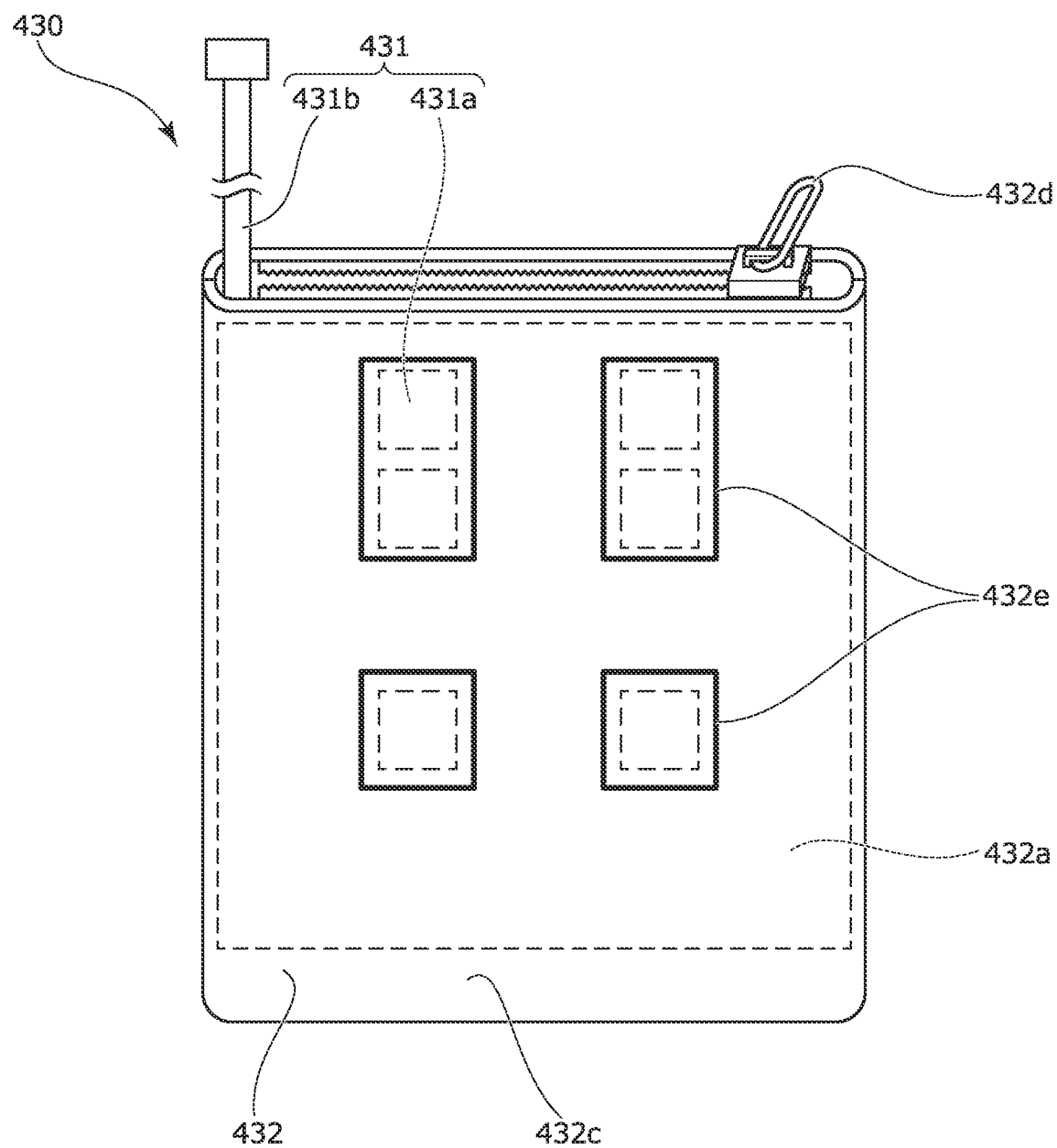
FIG. 9 is a front view of a sensor unit of a wired type.

As illustrated in FIGS. 8 and 9, the sensor unit 430 includes mainly a sensor module 431, and a sensor holder 432 that has a cushion shape and holds the sensor module 431 thereinside, and is detachably attached to each of a seat cushion 401 and a seat back 402 (attached portion).

Hereinafter, the sensor unit 430 provided in the seat cushion 401 will be described.

Figure 10A:
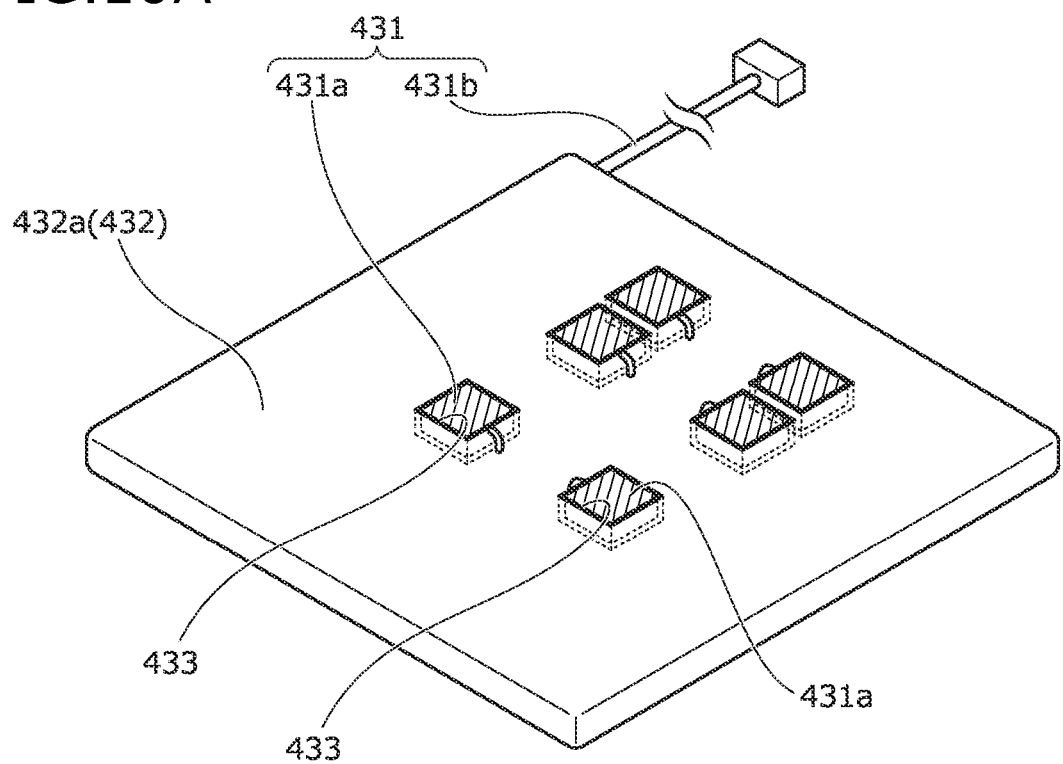
FIG. 10A is a perspective view illustrating front surfaces of a sensor module and a cushion material.
Figure 10B:
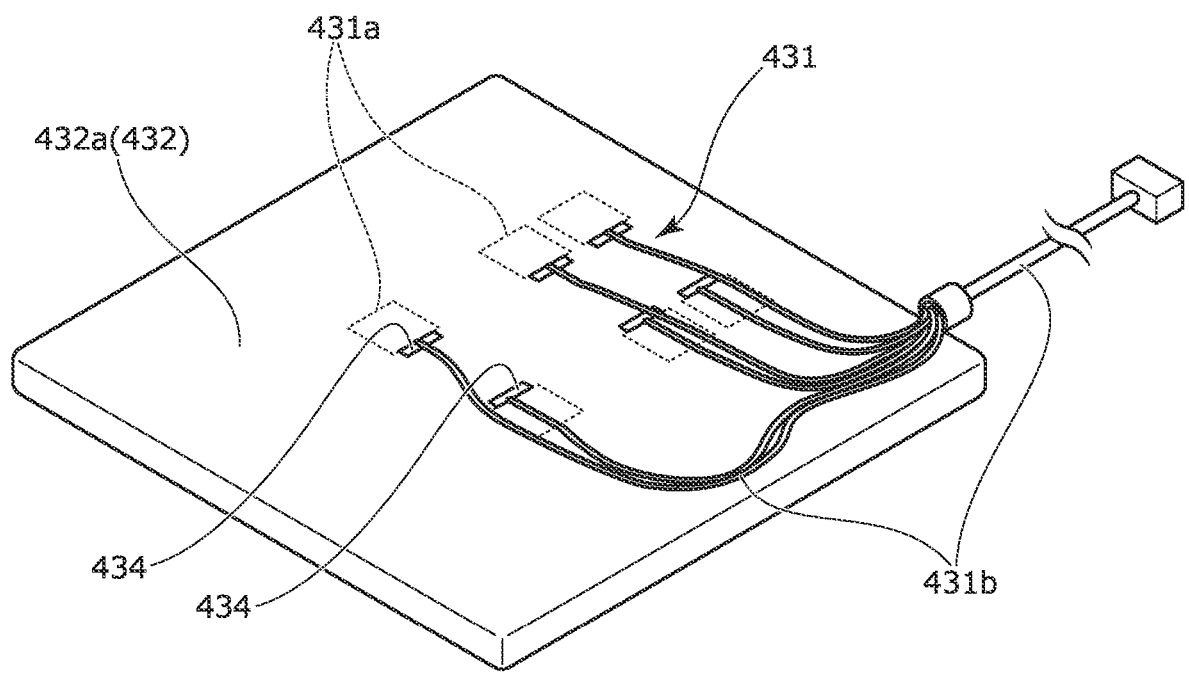
FIG. 10B is a perspective view illustrating back surfaces of the sensor module and the cushion material.

As illustrated in FIGS. 9, 10A, and 10B, the sensor module 431 includes a plurality of biological sensors 431a, and a wired communication unit 431b that are connected to the plurality of biological sensors 431a to transmit a detected biological signal to the outside.

The biological sensors 431a are planar pressure sensors, and are disposed at intervals in the seat width direction and in the seat front to rear direction in a total of six locations corresponding to positions at which the seated occupant is abuttable against the biological sensors 431a. Incidentally, in order to increase the detection accuracy of the sensor, the biological sensors 431a are disposed in four locations at positions corresponding to the buttocks of the seated occupant.

The wired communication unit 431b includes conductive wires that connect the biological sensors 431a and an ECU which is not illustrated and is provided in the seat cushion 401, and a harness that is a bundle of the conductive wires.

As illustrated in FIGS. 8 and 9, the sensor holder 432 is a piece of cushion, and includes mainly a cushion material 432a that has a substantially flat plate shape and supports the plurality of biological sensors 431a from below, and a cover material 432c that has a bag shape and stores the sensor module 431 and the cushion material 432a thereinside.

Seat attachment portions 432f (hook-and-loop fasteners) which can be attached to a front surface of the seat cushion 401 are attached to back surfaces of four corners of the sensor holder 432.

A front surface of the cushion material 432a is provided with a plurality of storage recessed portions 433 which store the biological sensors 431a, and slit holes 434 which have a wire shape and are provided adjacent to the storage recessed portions 433, respectively, and through which the wired communication units 431b (conductive wires) penetrate.

In the above configuration, the wired communication unit 431b (conductive wires) penetrates through the slit hole 434 from the biological sensor 431a to extend to a back surface of the cushion material 432a. In addition, a plurality of the wired communication units 431b are bundled on the back surface of the cushion material 432a to extend as a harness.

Incidentally, the cushion material 432a may have a multi-layer structure. In that case, layers may be fixed to each other with an adhesive or the like, and a pedestal made of a transparent resin may be provided as an underlying layer. Since the transparent resin is adopted, the wiring of the wired communication unit 431b can be easily observed.

Incidentally, the length and the width of the slit hole 434 can be appropriately adjusted.

The cover material 432c is formed by superimposing a pair of skin covers on top of each other in a surface-to-surface manner, forming one end portion as an opening portion, and sewing the remaining end portion, and a zip fastener is provided on an inner surface of the opening portion of the cover material 432c, as a cover closing portion 432d.

The internal space of the cover material 432c is formed with the same size as that of the outer shape of the cushion material 432a, and the plurality of biological sensors 431a are stored on a front surface of the cover material 432c without being shifted in position.

A positioning display portion 432e which displays the holding position of the sensor module 431 to the outside is formed in the front surface of the cover material 432c, as a rectangular sewing line.

Incidentally, in addition to the positioning display portion 432e, a positioning display portion which confirms the position of the sensor unit 430 in the front to rear direction (right to left direction) may be separately formed.

Even in the above configuration, the sensor unit which can be easily attached to and detached from a seating seat can be realized, and is a sensor unit that is replaceable in various conveyance seats.

In addition, with a relatively simple configuration, the plurality of biological sensors can be collectively attached to a seating seat, and can be positioned.

In the above configuration, as illustrated in FIG. 10A, the storage recessed portions 433 are formed in the front surface of the cushion material 432a, and meanwhile, storage recessed portions which store the wired communication units 431b may be also separately formed in the back surface of the cushion material 432a.

In such a case, when the biological sensors 431a and the wired communication units 431b are attached to the cushion material 432a, the front surface and the back surface of the cushion material 432a are substantially flush, so that the seating feeling of the seated occupant is good.

Incidentally, it is desirable that the front surface and the back surface of the cushion material 432a are substantially flush, but the front surface and the back surface are not particularly limited thereto, and a portion of the cushion material 432a, to which the biological sensor 431a is attached, may slightly protrude or may be slightly recessed.

In the above configuration, as illustrated in FIG. 10A, the storage recessed portions 433 which position the biological sensors 431a are formed in the front surface of the cushion material 432a, and meanwhile, as an alternative positioning method, predetermined markings (triangular markings) may be applied or a jig may be used.

Sixth Embodiment of Seat Equipped with Sensor Unit

Next, a seat S6 equipped with a sensor unit in a sixth embodiment will be described with reference to FIGS. 11 to 13.

In the seat S6 equipped with a sensor unit, the configuration of a seat attachment portion 533 of a sensor unit 530 differs mainly from that in the seat S5 equipped with a sensor unit.

The sensor unit 530 includes a sensor module 531 including biological sensors 531a, and a sensor holder 532 that has a cushion shape and holds the sensor module 531 therein-side, and is detachably attached to each of a seat cushion 501 and a seat back 502 (attached portion).

Hereinafter, the sensor unit 530 provided in the seat back 502 will be described.

The sensor holder 532 is a piece of cushion.

The seat attachment portion 533 which can be attached to a front surface of the seat back 502 is attached to both end portions in a longitudinal direction (up to down direction) of the sensor holder 532.

The seat attachment portion 533 includes an upper cover 533a that is attached to an upper end portion of the sensor holder 532 by sewing to extend toward a headrest 503 side, and a lower cover 533b that is attached to a lower end portion of the sensor holder 532 by sewing to extend toward a seat cushion 501 side.

A pair of insertion holes 534 into which a pair of pillars 503a of a headrest 503 are inserted are formed in a substantially central portion in an extending direction of the upper cover 533a.

In addition, an engaging hook 535 (engagement member) which has a substantially J-shaped cross section and is long in the seat width direction is fixed to an extending end portion of the upper cover 533a with an adhesive.

An engagement member 536 (engaged member) which has a rectangular shape and is long in the seat width direction is fixed to an extending end portion of the lower cover 533b with an adhesive.

The engaging hook 535 and the engagement member 536 are trim cords made of resin, and the engaging hook 535 can be hooked to the engagement member 536.

Figure 12:
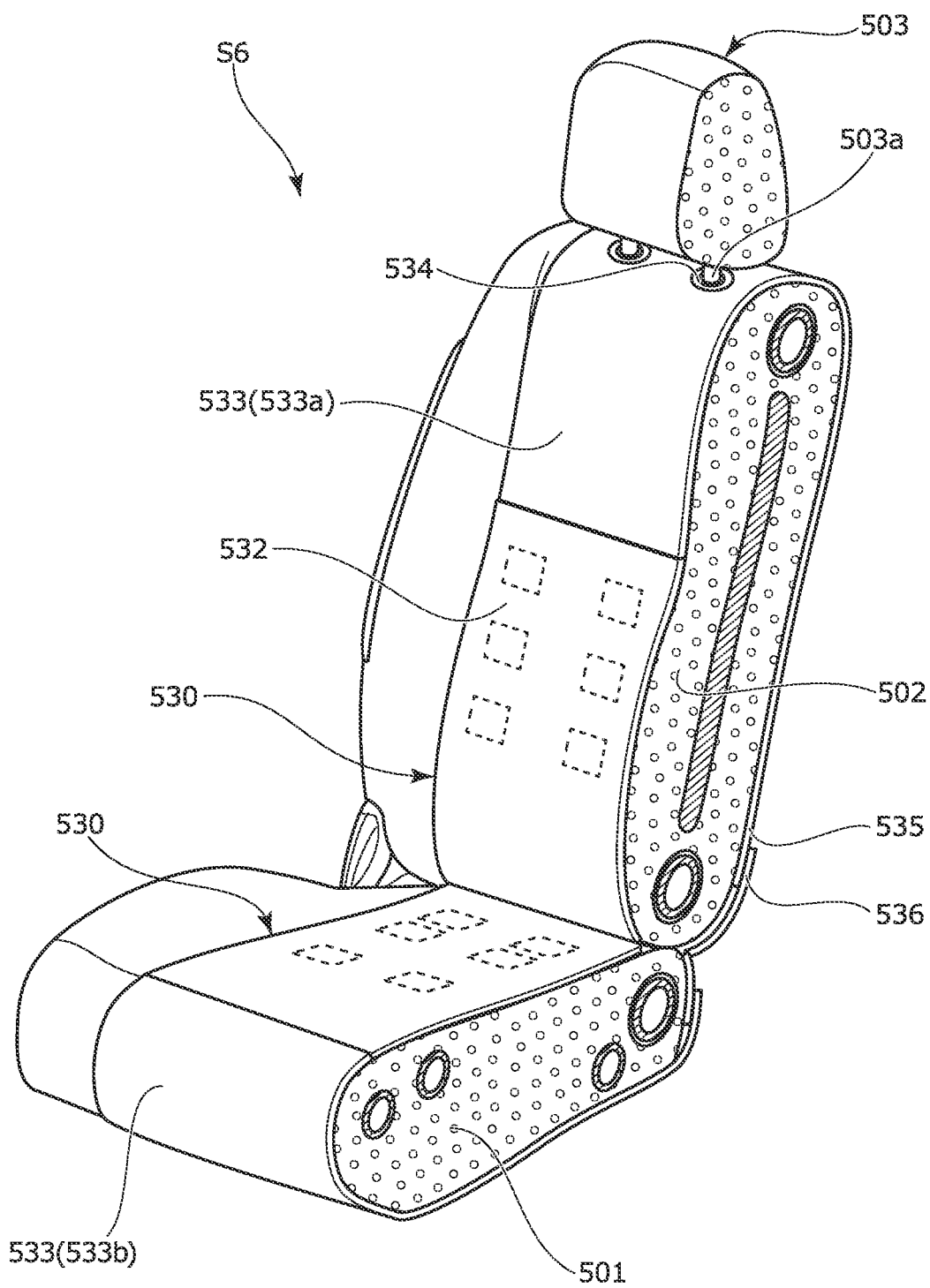
FIG. 12 is a perspective view of the seat equipped with a sensor unit.

In the above configuration, in order to attach the sensor unit 530 to the seat back 502, first, as illustrated in FIG. 12, the sensor unit 530 is attached such that the seat back 502 is covered with the seat attachment portion 533. Specifically, a front surface, an upper surface, a bottom surface, and a rear surface of the seat back 502 are covered with the upper cover 533a and the lower cover 533b.

At this time, the pillars 503a of the headrest 503 are inserted into the insertion holes 534 of the upper cover 533a.

Figure 13:
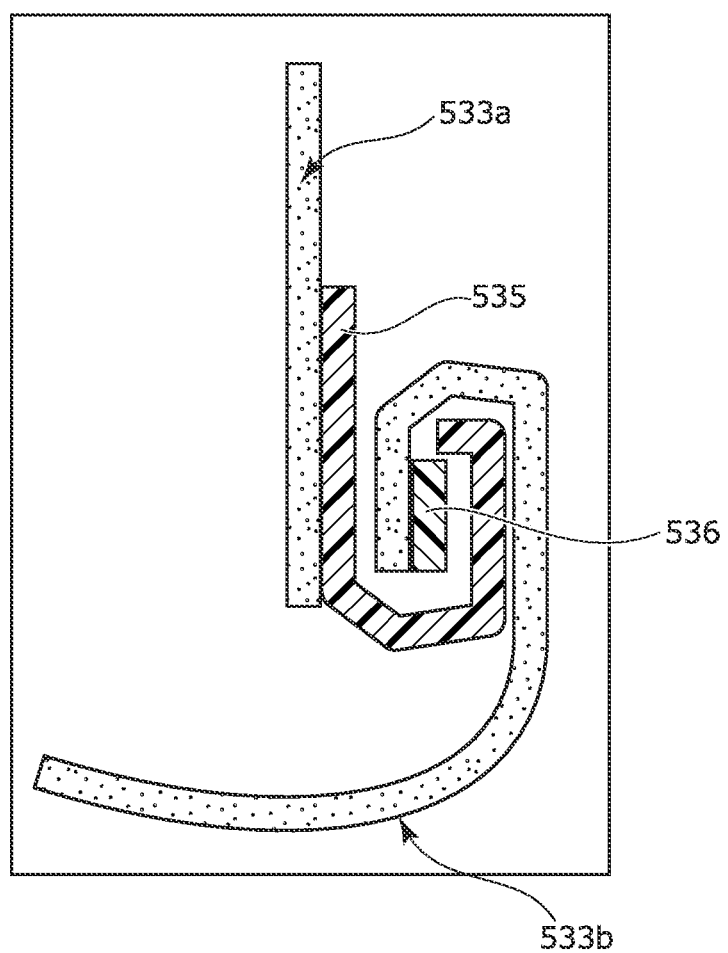
FIG. 13 is a key portion enlarged view of a sensor unit, and is a view illustrating a seat attachment portion with respect to a seat back (seat cushion).

Then, as illustrated in FIG. 13, in a lower end portion of a back surface of the seat back 502, the engaging hook 535 of the upper cover 533a is hooked to the engagement member 536 of the lower cover 533b.

Incidentally, a method for attaching the sensor unit 530 to the seat cushion 501 is similar.

Specifically, as illustrated in FIG. 12, an upper surface, a front surface, a bottom surface, and a rear surface of the seat cushion 501 are covered with the seat attachment portion 533.

Then, as illustrated in FIG. 13, in a rear end portion of the seat cushion 501, the engaging hook 535 of the rear cover 533a is hooked to the engagement member 536 of the front cover 533b.

Even in the above configuration, the sensor unit which can be easily attached to and detached from a seating seat can be realized, and is a sensor unit that is replaceable in various conveyance seats.

Seventh Embodiment of Seat Equipped with Sensor Unit

Figure 14:
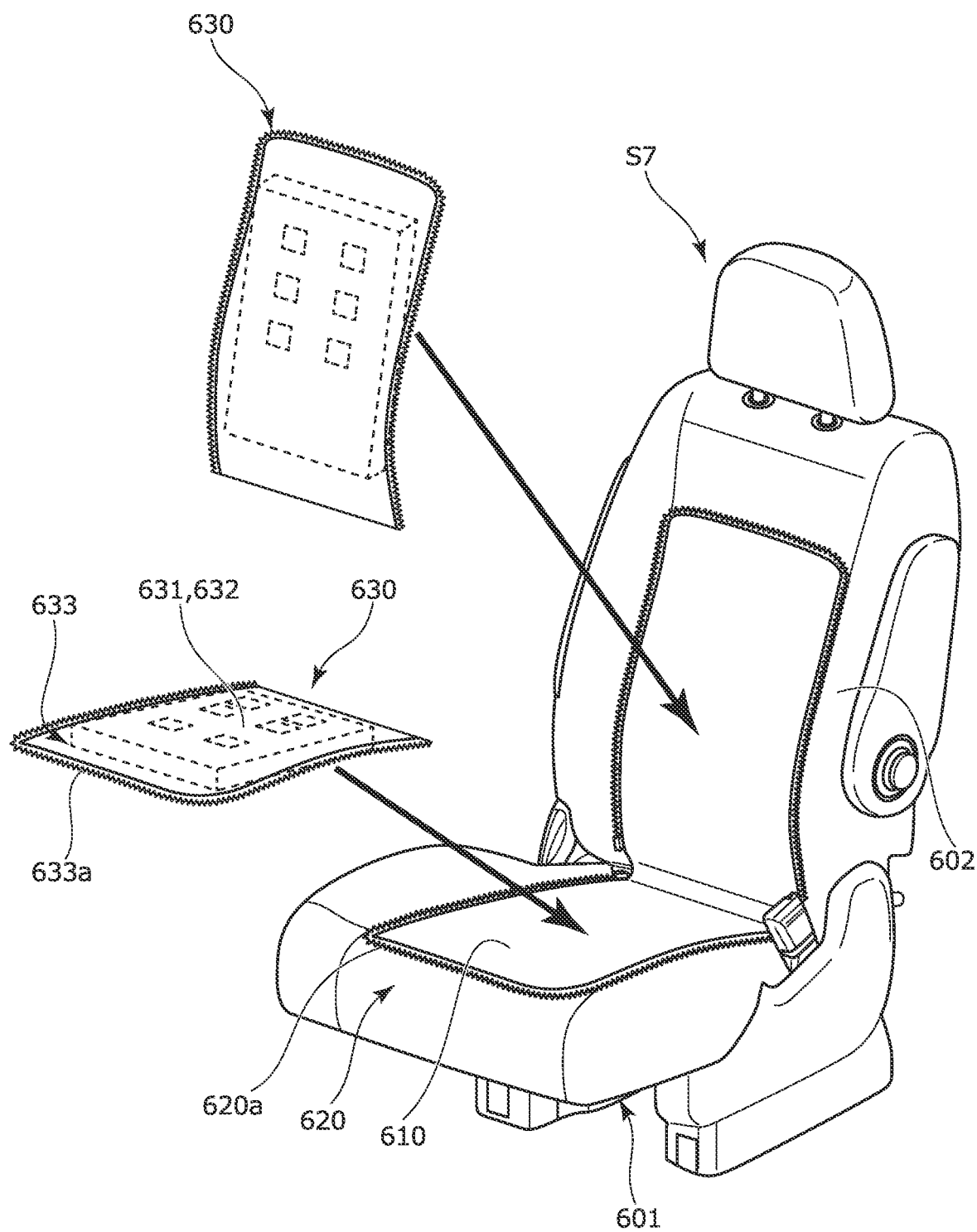
FIG. 14 is an exploded perspective view of a seat equipped with a sensor unit in a seventh embodiment.

Next, a seat S7 equipped with a sensor unit in a seventh embodiment will be described with reference to FIG. 14.

In the seat S7 equipped with a sensor unit, the configuration of a seat attachment portion 633 of a sensor unit 630 differs from that in the seat S6 equipped with a sensor unit.

The sensor unit 630 includes mainly a sensor module 631; a sensor holder 632 that has a cushion shape and holds the sensor module 631 thereinside; and the seat attachment portion 633 that is attached to a front surface of the sensor holder 632 to be attachable to a seat cushion 601 (seat back 602).

Hereinafter, the sensor unit 630 provided in the seat cushion 601 will be described.

The seat attachment portion 633 is a skin cover that is long and is attached to the front surface of the sensor holder 632 by sewing or with an adhesive, and a cushion pad 610 is covered with a part of a skin material 620 of the seat cushion 601.

A zip fastener 633a is provided throughout a front end portion and both end portions in the seat width direction of an outer edge of the seat attachment portion 633, and meshes with a zip fastener 620a provided in the skin material 620 as a set, so that the sensor unit 630 can be attached to the seat cushion 601.

In this case, the zip fastener 633a is not provided in a rear end portion of the outer edge of the seat attachment portion 633. In such a case, the seat S7 equipped with a sensor unit can be easily produced, and the work of assembling the sensor unit 630 is also facilitated.

With the above configuration, the sensor unit 630 can be attached to the seat cushion 601 by changing the skin material.

Eighth Embodiment of Seat Equipped with Sensor Unit

Figure 15:
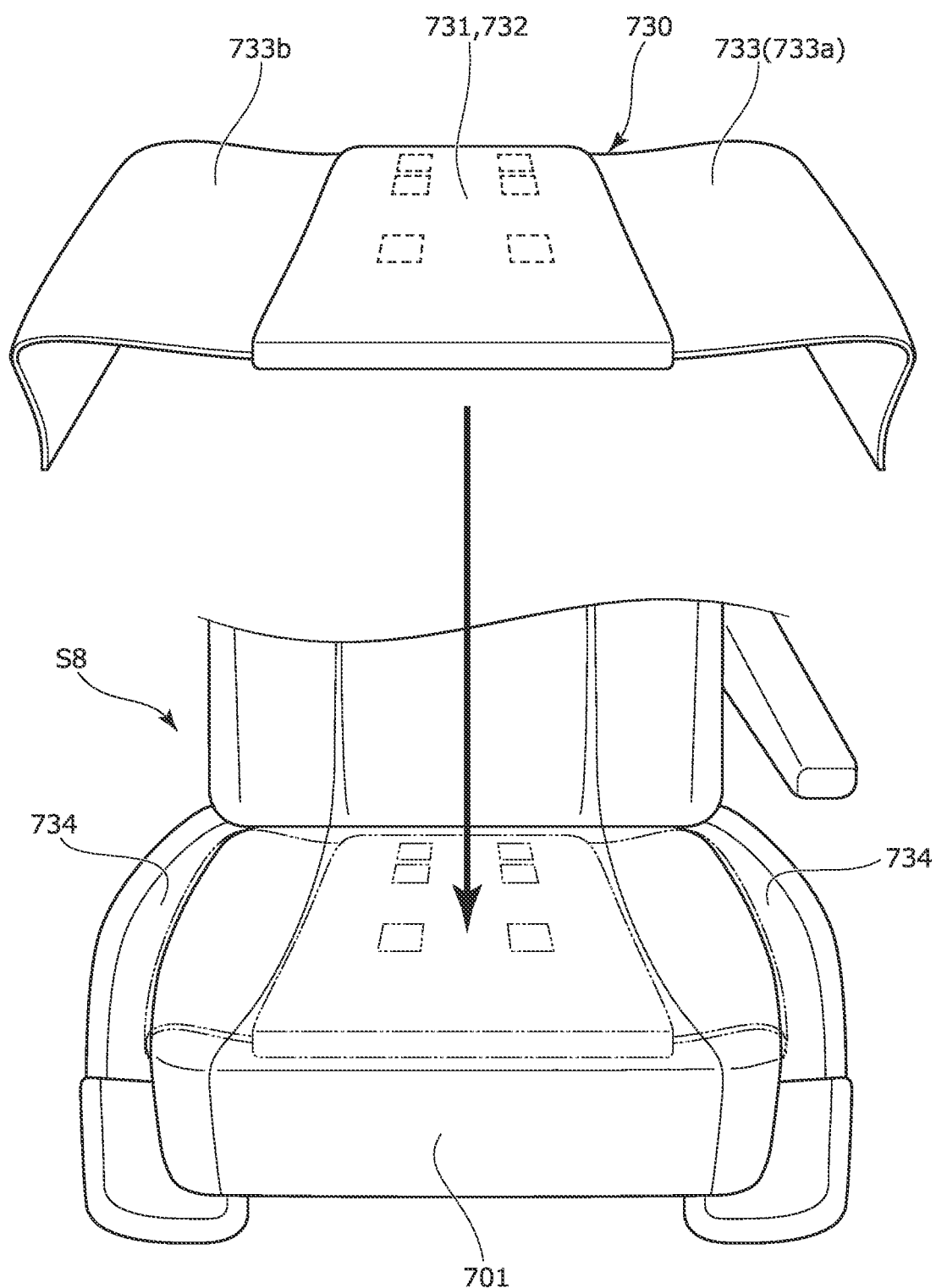
FIG. 15 is an exploded perspective view of a seat equipped with a sensor unit in an eighth embodiment.

Next, a seat S8 equipped with a sensor unit in an eighth embodiment will be described with reference to FIG. 15.

In the seat S8 equipped with a sensor unit, the configuration of a seat attachment portion 733 of a sensor unit 730 differs from that in the seat S6 equipped with a sensor unit.

The sensor unit 730 is fitted with a sensor module 731; a sensor holder 732 that has a cushion shape and holds the sensor module 731 thereinside; and the seat attachment portion 733 that is attached to both end portions in a width direction (seat width direction) of the sensor holder 732 to be attachable to a seat cushion 701.

Incidentally, the seat S8 equipped with a sensor unit includes protective covers 734 on the right and left sides, which are made of resin and protect the seat cushion 701 from outside in the seat width direction.

The seat attachment portion 733 includes a right cover 733b and a left cover 733a that are attached to both right and left end portions of the sensor holder 732 by sewing to extend outward in the seat width direction.

Each of extending end portions of the left cover 733a and the right cover 733b is interposed between the seat cushion 701 and the protective cover 734, so that the sensor unit 730 can be attached to the seat cushion 701.

Ninth Embodiment of Seat Equipped with Sensor Unit

Figure 16:
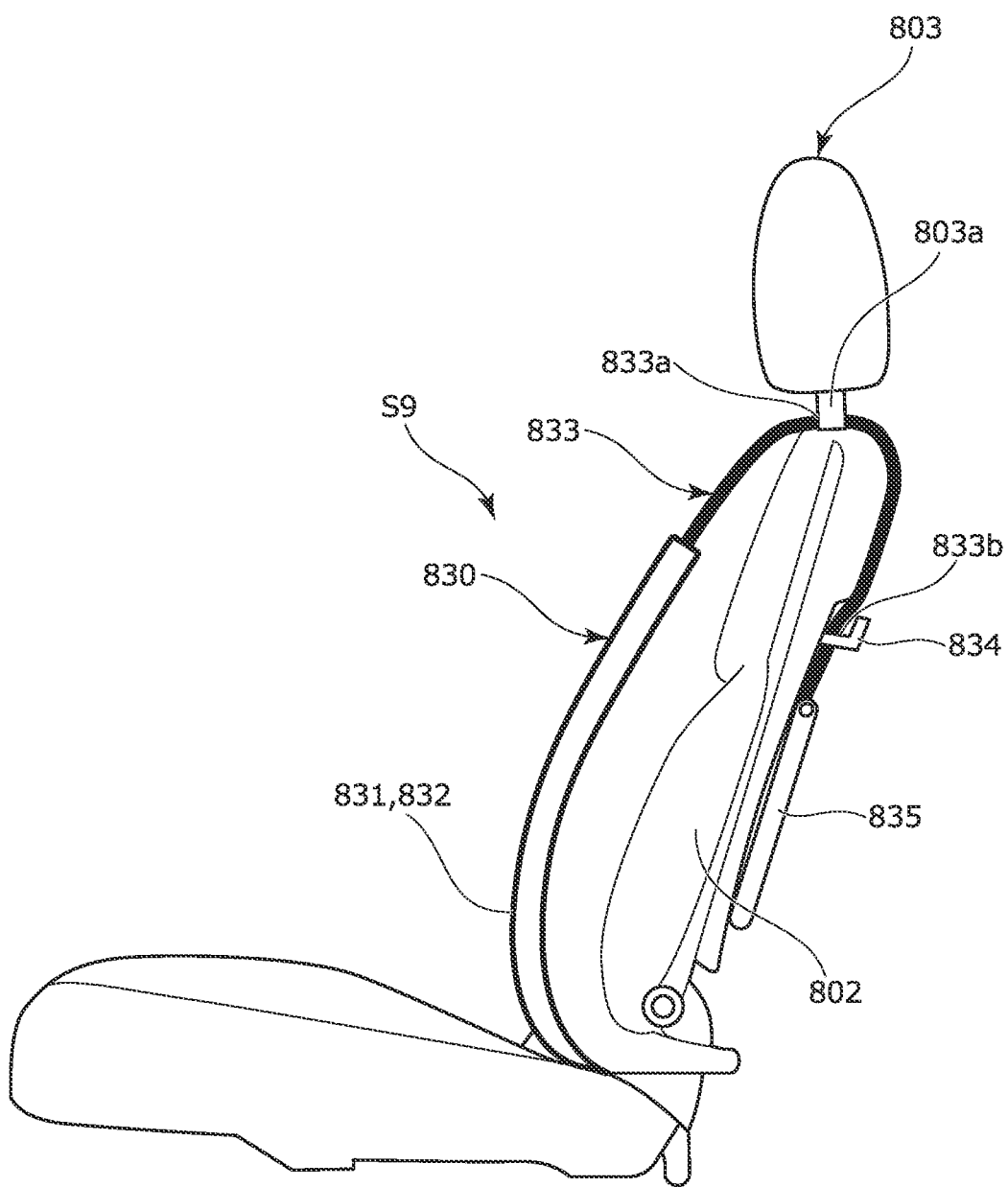
FIG. 16 is an exploded perspective view of a seat equipped with a sensor unit in a ninth embodiment.

Next, a seat S9 equipped with a sensor unit in a ninth embodiment will be described with reference to FIG. 16.

In the seat S9 equipped with a sensor unit, the configuration of a seat attachment portion 833 of a sensor unit 830 differs from that in the seat S6 equipped with a sensor unit.

The sensor unit 830 is fitted with a sensor module 831; a sensor holder 832 that has a cushion shape and holds the sensor module 831 thereinside; and the seat attachment portion 833 that is attached to an upper end portion of the sensor holder 832 to be attachable to a seat back 802.

Incidentally, the seat S8 equipped with a sensor unit includes a hook 834 that has a J shape and is attached at an upper position on a back surface of the seat back 802, and a table 835 that is disposed at a position lower than the hook 834 to be rotatably attached to the seat back 802.

The seat attachment portion 833 is a long cover that is attached to the upper end portion of the sensor holder 832 by sewing to extend upward, and includes a pair of insertion holes 833a into which a pair of pillars 803a of a headrest 803 are inserted, and a hook hole 833b which is hooked to the hook 834.

In addition, an extending end portion of the seat attachment portion 833 is interposed between the seat back 802 and the table 835.

With the above configuration, the sensor unit 830 can be attached to the seat back 802 by using an existing component.

Incidentally, the sensor unit 830 may be attached to the seat back 802 by using an armrest as an existing component.

Tenth and Eleventh Embodiments of Seat Equipped with Sensor Unit

Figure 17:
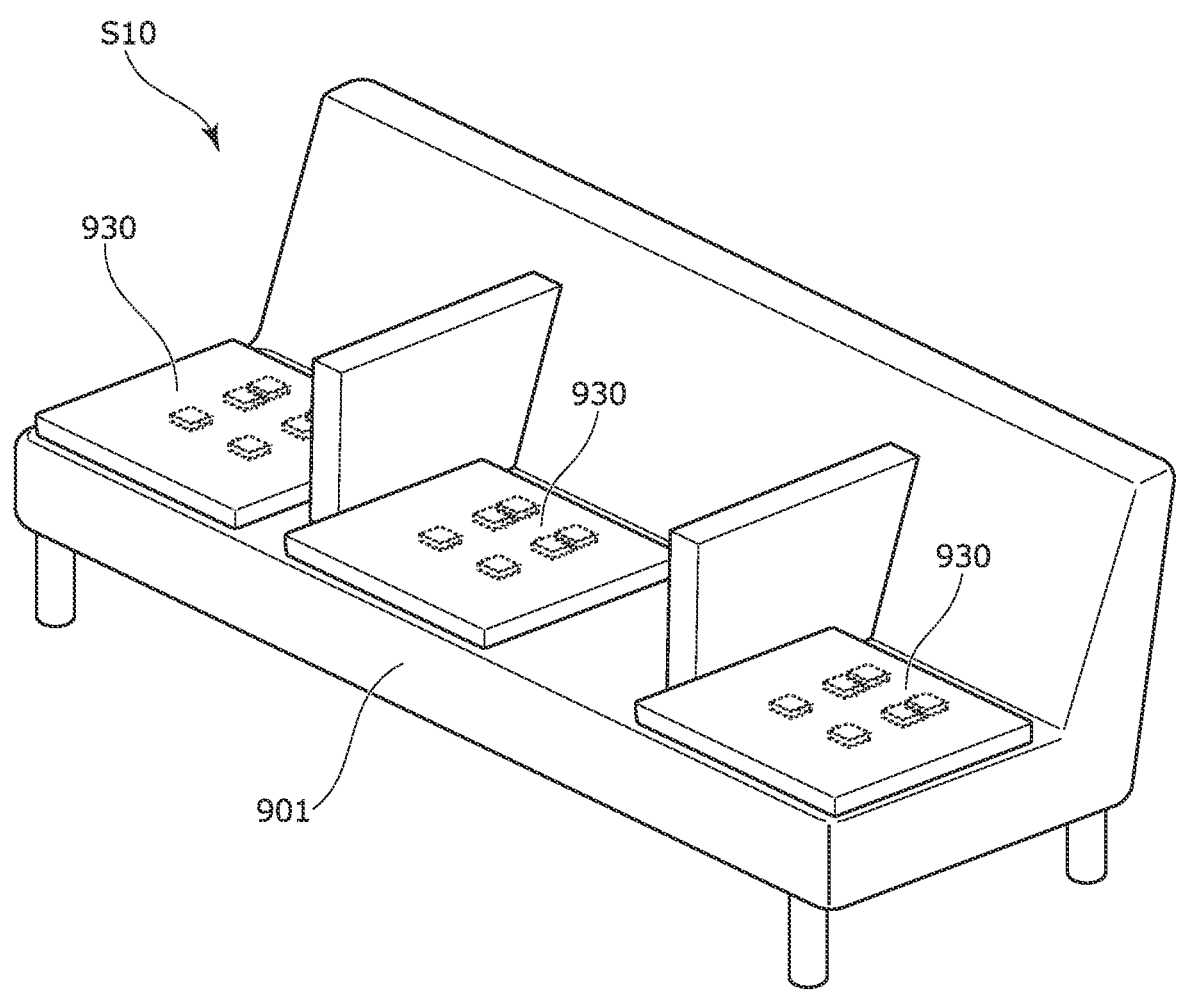
FIG. 17 is an exploded perspective view of a seat equipped with a sensor unit in a tenth embodiment.
Figure 18:
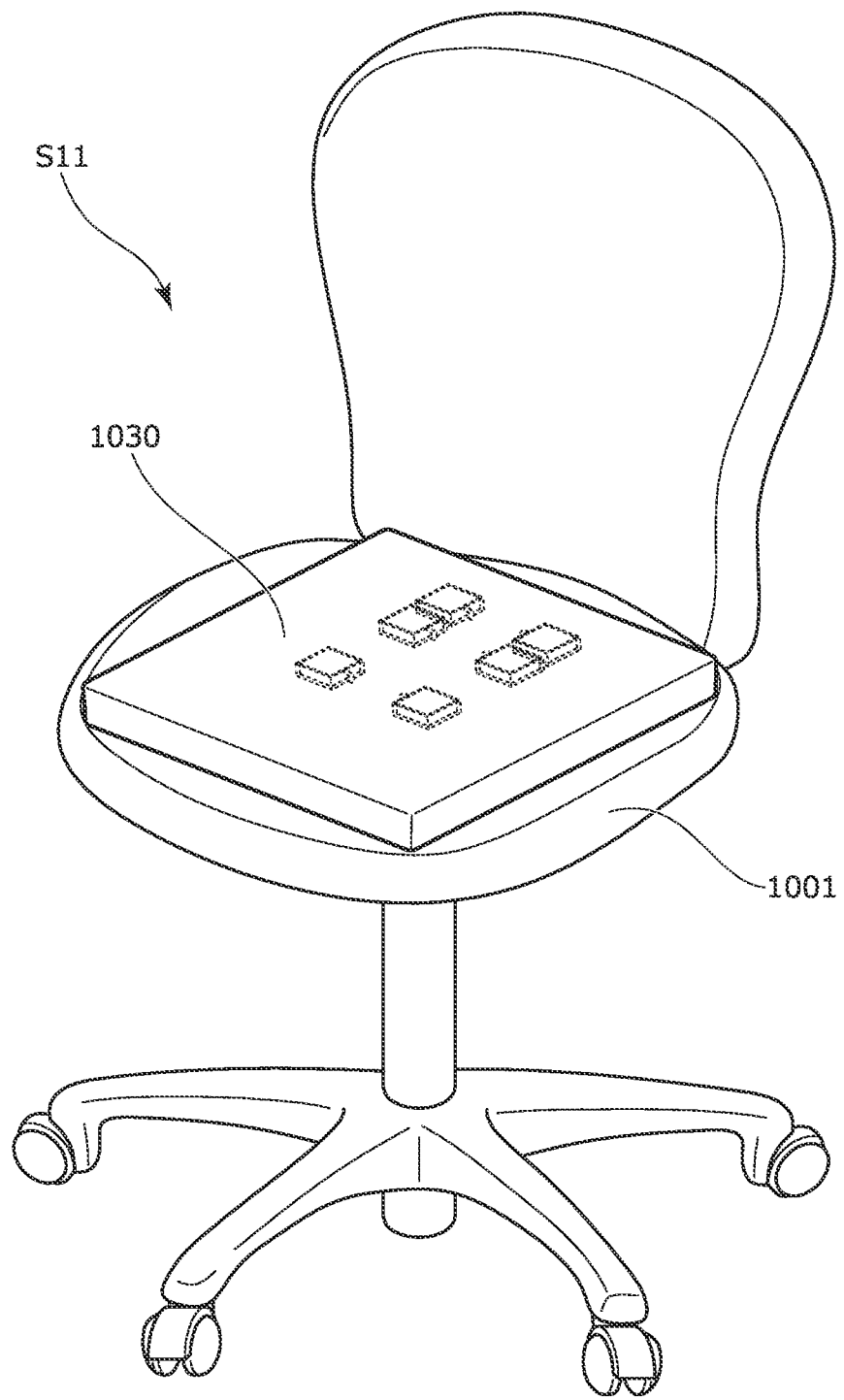
FIG. 18 is an exploded perspective view of a seat equipped with a sensor unit in an eleventh embodiment.

Next, a seat S10 equipped with a sensor unit and a seat S11 equipped with a sensor unit in tenth and eleventh embodiments will be described with reference to FIGS. 17 and 18.

The seat S10 equipped with a sensor unit is a sofa type seating seat. A sensor unit 930 having a cushion shape is detachably attached to a front surface of a seat cushion 901 of the seat S10.

The seat S11 equipped with a sensor unit is an office chair type seating seat.

A sensor unit 1030 having a cushion shape is detachably attached to a front surface of a seat cushion 1001 of the seat S11.

The sensor units 930 and 1030 may be attached to the seat cushions 901 and 1001 using, for example, hook-and-loop fasteners, respectively.

Other Embodiments

In the above embodiment, as illustrated in FIG. 1, the sensor unit 30 is attached inside the seat cushion 1, but the attachment location is not particularly limited thereto and can be changed. The sensor unit 30 may be attached inside the seat back 2, may be attached inside the headrest 3, or may be attached inside or outside the armrest 4. In addition, the sensor unit 30 may be attached inside or outside an ottoman not illustrated.

In addition, the sensor unit 30 is attached to the seat in which the seated occupant is seated, but the present invention is not particularly limited thereto, and the sensor unit 30 may be attached inside or outside an object against which a human is abuttable.

In the above embodiment, as illustrated in FIG. 2B, the sensor unit 30 includes the seat attachment portion 32f (a hook-and-loop fastener or a double-faced tape) that can be attached to the surface of the skin material 20 (skin pockets 21 to 24) of the seat cushion 1, but the type of the seat attachment portion 32f is not particularly limited to the hook-and-loop fastener or the double-faced tape, and can be changed.

Figure 19A:
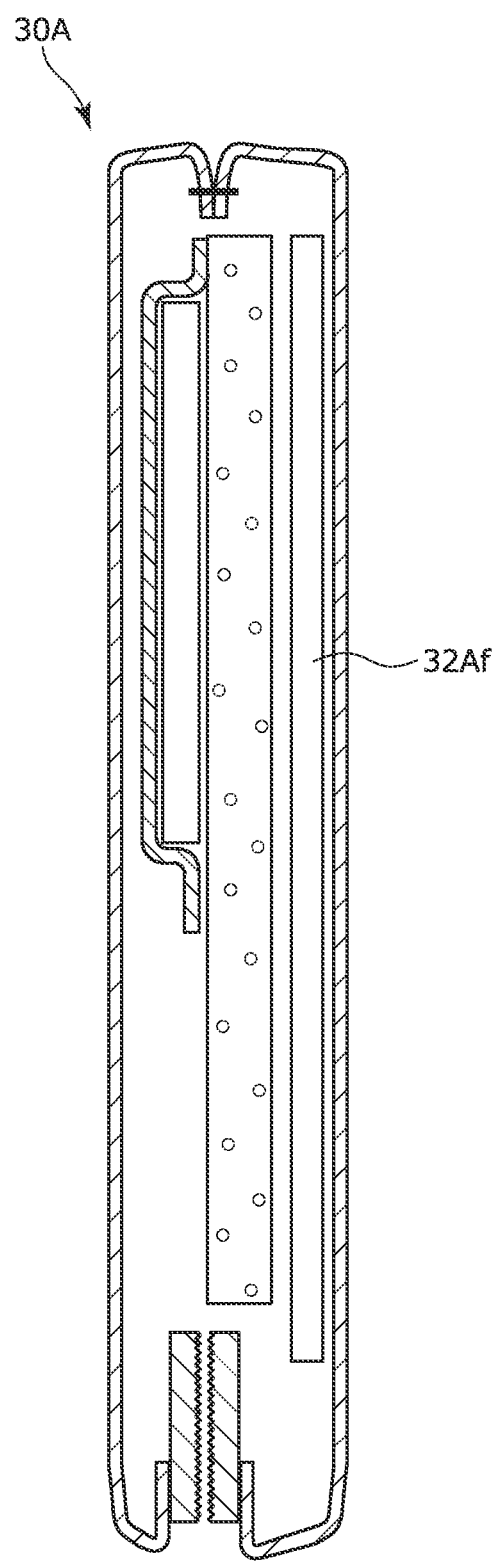
FIG. 19A is a view illustrating another embodiment of a seat attachment portion of a sensor unit.

Specifically, as illustrated in FIG. 19A, a sensor unit 30A may include a rectangular plate-shaped magnet as a seat attachment portion 32Af. With such a configuration, the sensor unit 30A is detachably attached to a metal wire (for example, a metal wire to which a skin material is hooked) provided in a cushion pad of a seat cushion or a seat back. Alternatively, the sensor unit 30A is detachably attached to a metal frame that is a skeleton of the seat cushion or the seat back.

Figure 19B:
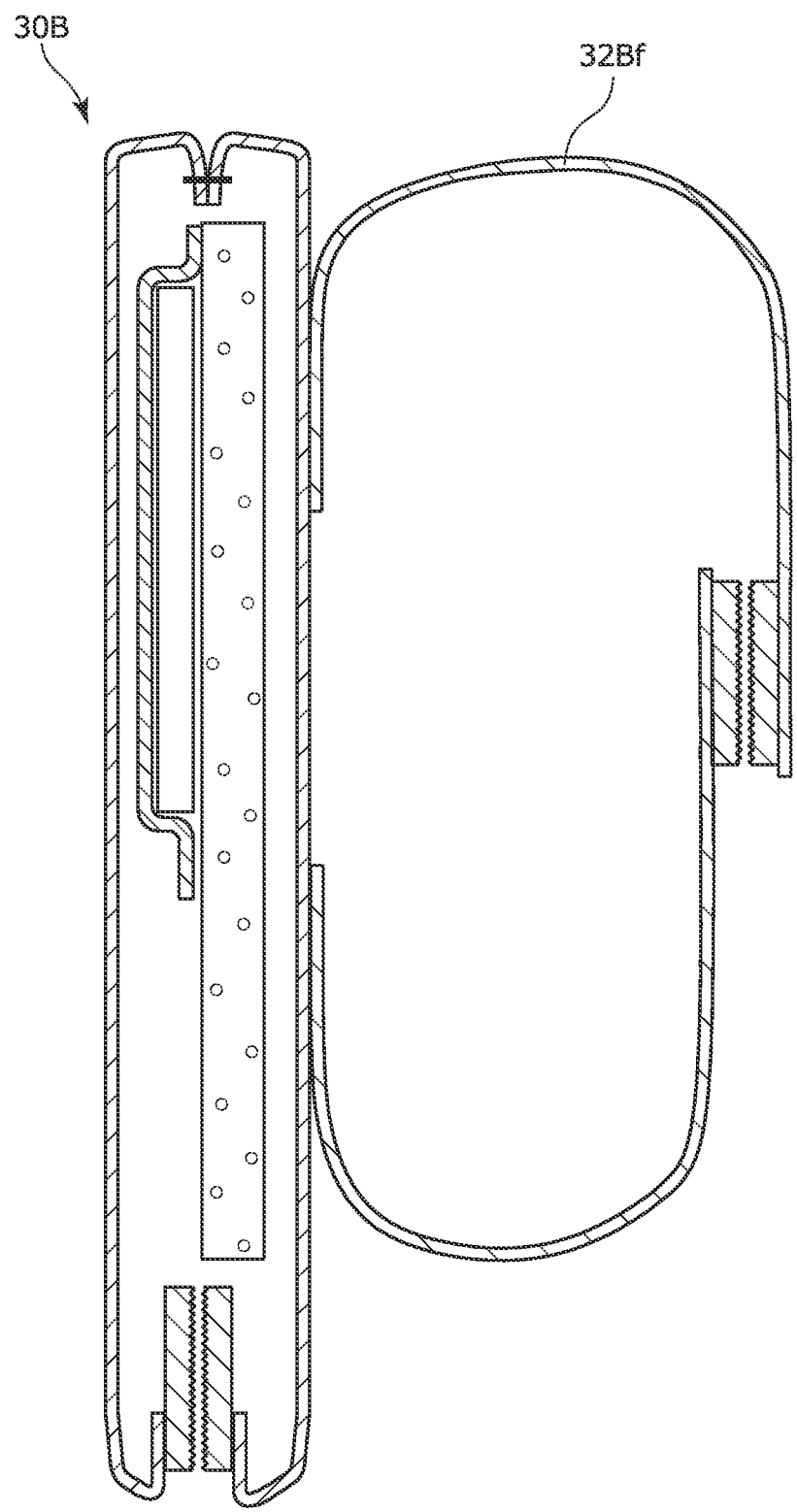
FIG. 19B is a view illustrating another embodiment of a seat attachment portion.

In addition, specifically, as illustrated in FIG. 19B, a sensor unit 30B may include an attachment band as a seat attachment portion 32Bf on an outer surface (back surface) thereof. With such a configuration, the seat attachment portion 32Bf is detachably attached to an outer surface of an armrest (attached portion) with the armrest interposed between portions of the seat attachment portion 32Bf.

Figure 4:
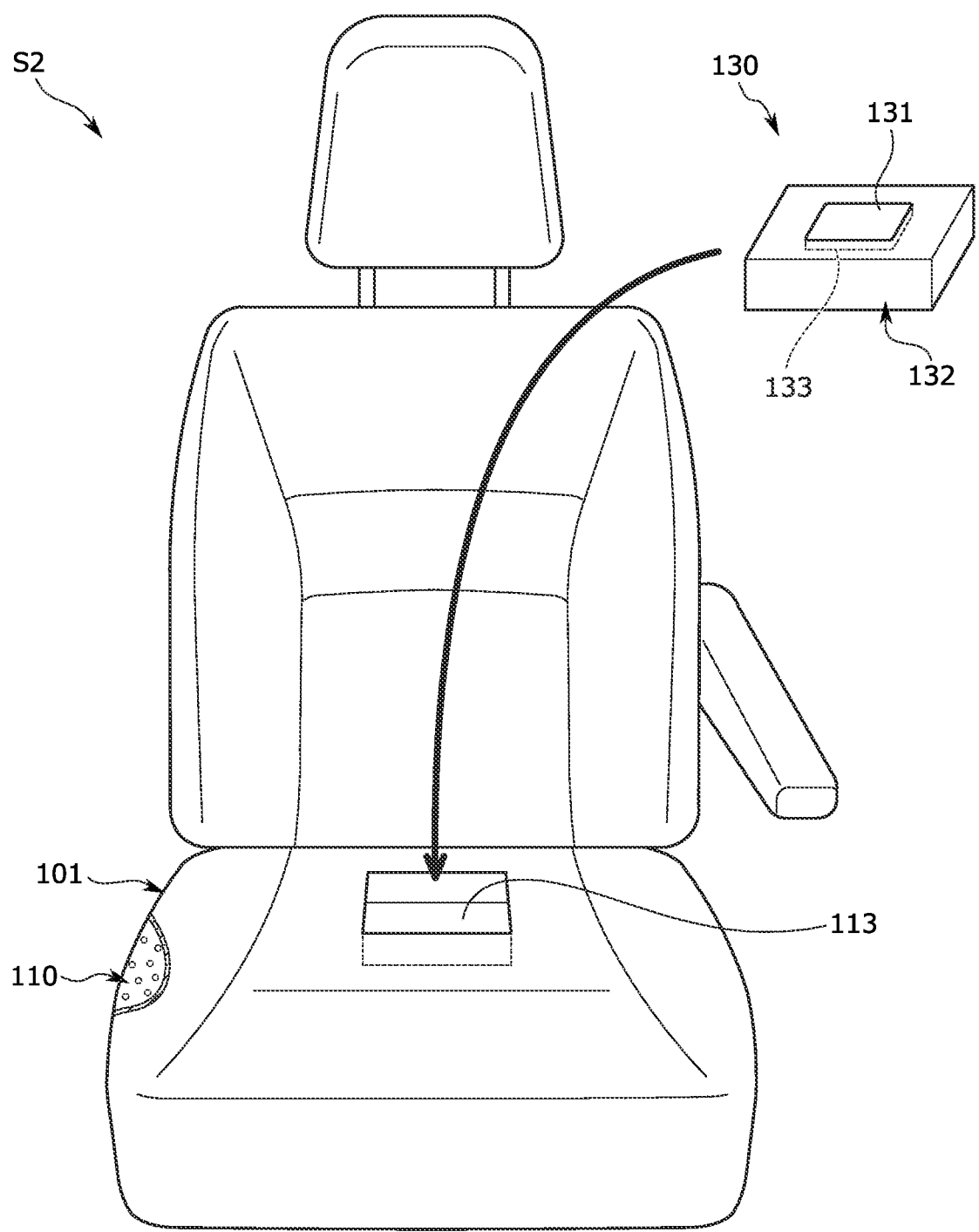
FIG. 4 is an external appearance perspective view of a seat equipped with a sensor unit in a second embodiment.

In the above embodiment, as illustrated in FIG. 4, the sensor module 131 (biological sensor) is stored on the front surface of the sensor holder 132 having a block shape, but is not particularly limited thereto, and may be stored in the storage recessed portion provided on the back surface of the sensor holder 132.

In that case, the sensor module 131 (biological sensor) is disposed to be interposed between the sensor holder 132 and the cushion recessed portion 113, which is provided in the seat cushion 101 (cushion pad 110), in an up to down direction.

With such a configuration, the biological sensor can be more stably attached to the seat. In addition, when the thickness of the block of the sensor holder 132 is made as small as possible, the biological signal of the seated occupant can be more easily detected.

In the above embodiment, as illustrated in FIG. 8, the seat S5 equipped with a sensor unit includes the sensor unit 430 having a cushion shape, and meanwhile, the sensor unit 430 may further include charging means (charging unit) using wireless communication or wired communication, and may include a remaining amount display unit that displays remaining charge.

In addition, the sensor unit 430 may include a display processing unit that wirelessly communicates with a mobile phone of the seated occupant to cause a display unit of the mobile phone to display a predetermined directing screen based on sensing information.

In addition, the sensor unit 430 may further include a failure determination unit which determines whether or not a sensing function has a failure, and may include a failure notification unit (failure display unit) which notifies that a failure has occurred during failure. Incidentally, the failure display unit may be disposed at a position in front of a seating surface of the seated occupant in the seat.

In addition, the shape of the sensor unit 430 and the shape of the biological sensor 431a are not limited to a rectangular shape, and may be a triangular shape, a circular shape, or the like, and may be a shape that is easy to position.

In the above embodiment, as illustrated in FIG. 8, the sensor unit 430 is formed as a piece of cushion, and meanwhile, a pocket portion may be further provided on an outer surface or an inner surface of the cushion. In this case, an ECU, a battery, a tablet, or the like may be inserted into the pocket portion. Incidentally, the pocket portion may be detachably attached to a body portion of the sensor unit 430.

In the above embodiment, as illustrated in FIG. 8, the sensor unit 430 is detachably attached to the seat cushion 401. For this reason, the sensor holder 432 (cover material 432c) can be changed in design or washed independently.

On the other hand, the sensor unit 430 may be integrally attached to the seat cushion 401 (skin material 420). In such a case, electronic components inside the sensor unit 430 can be suitably protected (can be suppressed from being exposed to the outside).

Incidentally, when the sensor unit 430 is integrally attached to the skin material 420, after the cushion material 432a equipped with the biological sensors 431a illustrated in FIG. 10A is stored inside the cover material 432c, the cushion material 432a, the cover material 432c, and the skin material 420 are sewed together.

In the above embodiment, as illustrated in FIG. 8, the sensor unit 430 is attached to the seat cushion 401 and the seat back 402 to sense the seating pressure of the seated occupant, and meanwhile, other seat components may be further attached.

Specifically, the sensor unit 430 may be attached to an armrest, an ottoman, or the like.

In such a case, the sensor unit 430 can not only sense the seating pressure of the seated occupant, but also sense a motion of the hand or a motion of the leg of the seated occupant.

In addition, the sensor unit 430 may be able to reversibly sense the seating pressure of the seated occupant. In such a case, the sensor unit 430 can be turned inside out and attached on the seat cushion 401, so that another sensing information can be acquired.

In addition, even when the sensor unit 430 is attached reversely in the front to rear direction, or is attached reversely in the right to left direction, sensing may be possible. In that case, the biological sensors 431a may be disposed front to rear symmetrically (right to left symmetrically).

In addition, the sensor unit 430 is a piece of cushion, and meanwhile, may be foldable, for example, in two folds. When folding is performed, the biological sensors 431a or the wired communication units 431b may be disposed to avoid the fold. Alternatively, the biological sensors 431a or the wired communication units 431b may be purposely disposed to overlap the fold.

In the above embodiment, as illustrated in FIG. 10B, the plurality of wired communication units 431b (conductive wires) are bundled and extend on the back surface of the cushion material 432a, and meanwhile, the wiring direction of the wired communication units 431b (conductive wires) and the wiring direction of the harnesses can be appropriately changed.

In addition, the wired communication units 431b (harnesses) lead outward from the opening of the sensor holder 432, and meanwhile, the lead-out position of the wired communication units 431b may not be a corner of the opening of the sensor holder 432. Namely, the lead-out position may be located in a central portion of the opening of the sensor holder 432, or may be the position of a through-hole that is separately formed at a predetermined position in the sensor holder 432.

Figure 11:
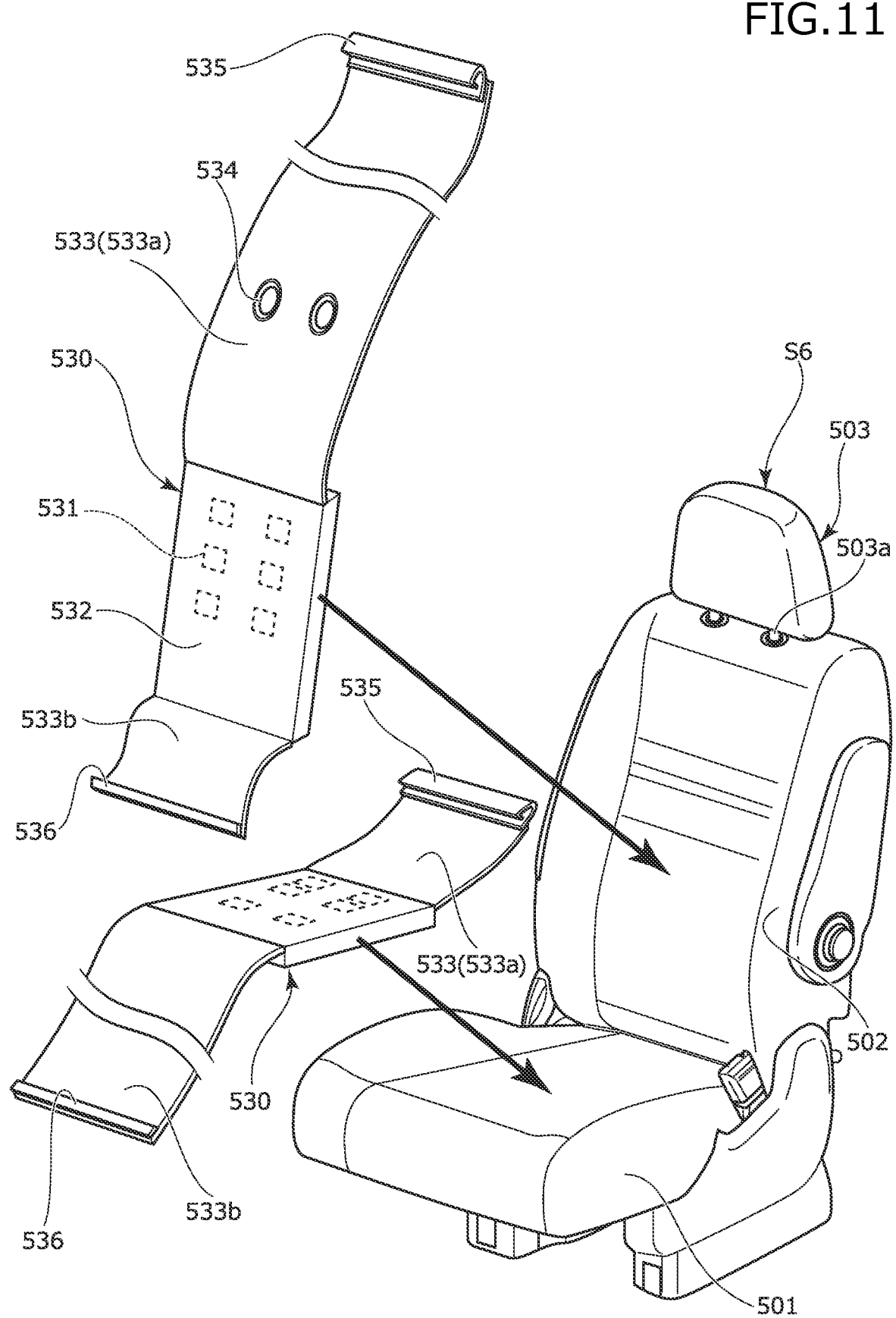
FIG. 11 is an exploded perspective view of a seat equipped with a sensor unit in a sixth embodiment.

In the above embodiment, as illustrated in FIG. 11, the sensor unit 530 is attached to the seat back 502, and meanwhile, the sensor unit 530 may be disposed at a position avoiding a reclining device not illustrated. Alternatively, the sensor unit 530 may be further hooked by using a component of the reclining device.

Figure 20A:
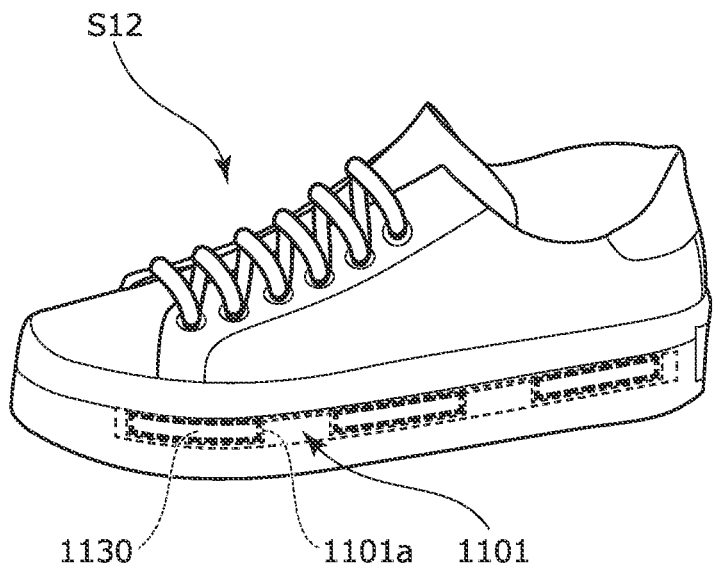
FIG. 20A is a perspective view of a shoe equipped with a sensor unit.
Figure 20B:
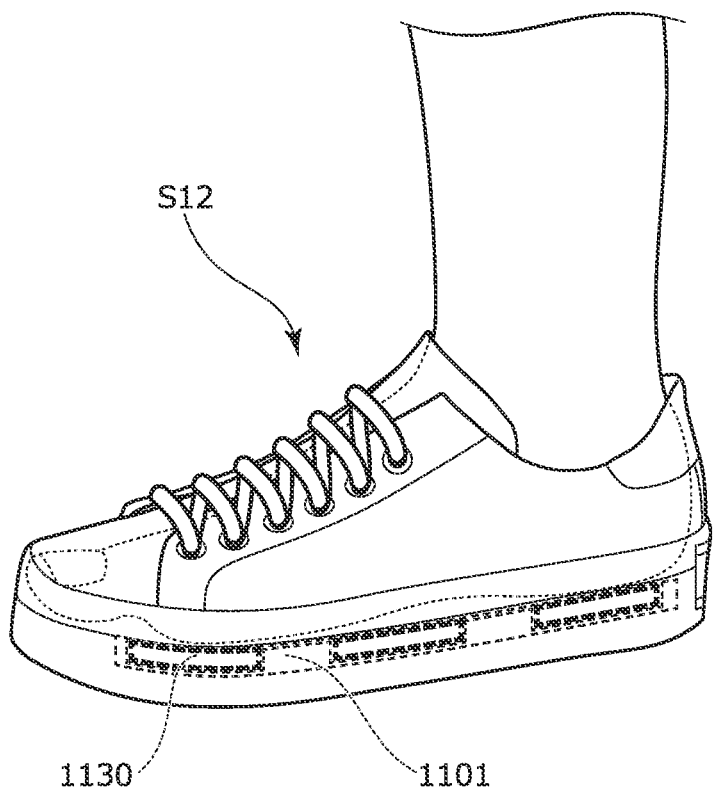
FIG. 20B is a perspective view of the shoe equipped with a sensor unit.

In the above embodiments, as illustrated in FIG. 1 to FIGS. 19A and 19B, the seats S1 to S11 each equipped with a sensor unit have been described; however, the present invention is not limited to the seating seat, and may be applied to, for example, a shoe S12 with a sensor unit illustrated in FIGS. 20A and 20B.

The shoe S12 with a sensor unit may include an insole 1101 (inner sole) equipped with a sensor unit 1130 inside the shoe.

Specifically, a plurality of the sensor units 1130 may be provided, and may be stored in storage recessed portions 1101a formed in an upper portion of the insole 1101, respectively.

In addition thereto, the present invention may be applied to an insert equipped with a sensor unit.

In the above embodiments, the vehicle seat used in automobiles has been described as a specific example; however, the present invention is not particularly limited thereto, and can be used for various seats such as work office chairs, wheelchairs, children's chairs for shopping carts, and the like, in addition to two-wheeled seats for two-wheeled vehicles, vehicle seats for trains, buses, and the like, and conveyance seats for airplanes, ships, and the like.

In the present embodiment, the sensor unit and the seat equipped with a sensor unit according to the present invention have been mainly described.

Meanwhile, the above embodiments are merely one example for facilitating the understanding of the present invention, and do not limit the present invention. The present invention can be changed or improved without departing from the concept of the present invention, and needless to say, the present invention includes equivalents thereof.

Particularly, the dispositions or configurations of the sensor units described in the above embodiments are merely one example, and do not limit the present invention.

<Display System and Vehicle>

Next, the invention relating to a display system, particularly to a display system including a projection device that operates in connection with the state of a seat inside a vehicle will be described with reference to FIGS. 21 to 28 and Table 1.

In the related art, a display system has been known in which a monitor is attached to a roof to display an image inside a vehicle. It has been disclosed that in a display described in a patent literature (JP 2015-09820317), the position of a conveyance seat is determined by a sensor, and the position of the display of a conveyance is automatically adjusted based on the determination.

In the display system described in the patent literature, in order to change the position of the display while supporting the display itself, it is required to provide a large-scale device that allows the display to move inside a vehicle, for example, to provide a rail or the like on a roof. However, the separate attachment of the large-scale device which attaches the display to the inside of the vehicle causes an increase in cost, which is a problem. A system which displays an image inside the vehicle in a simpler manner has been desired.

Therefore, the present invention realizes a display system in which a large-scale device is not provided inside a vehicle and the state of a seat and the display position of an image are linked to each other.

Figure 21:
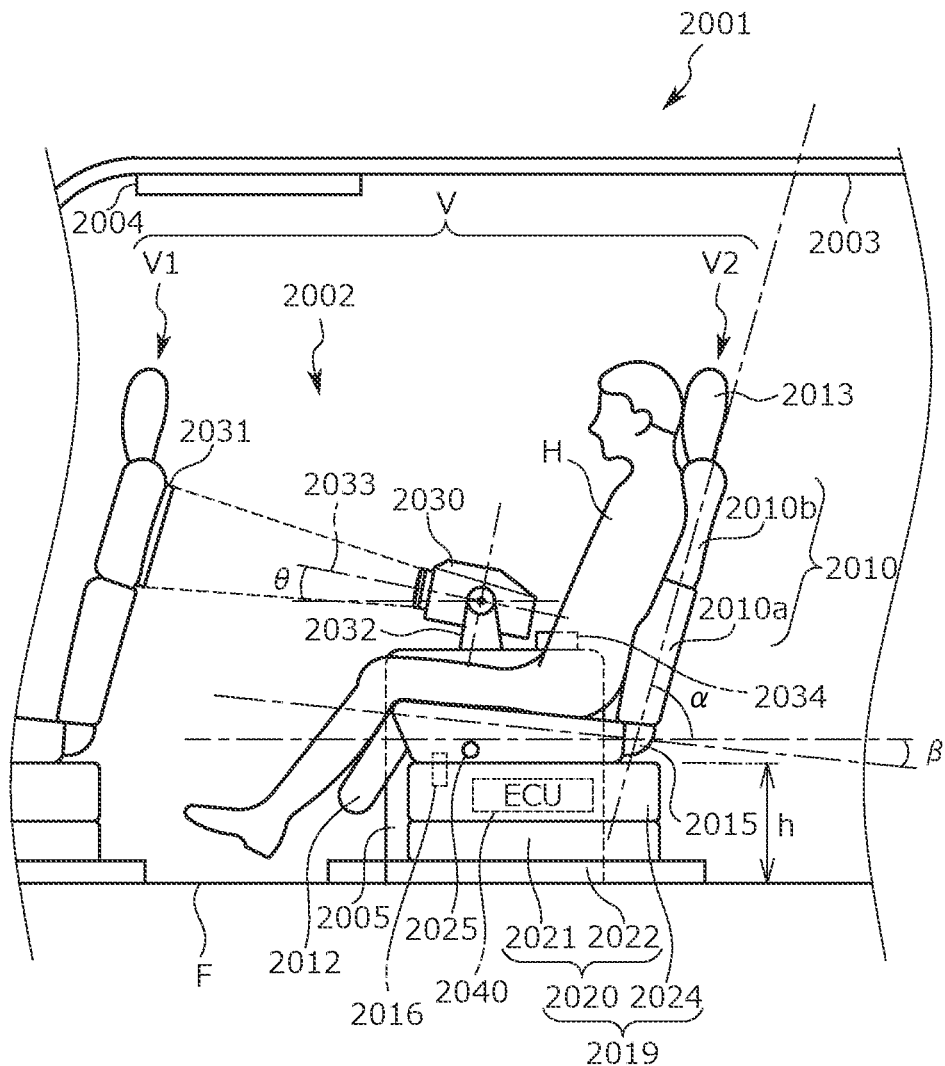
FIG. 21 is a side view schematically illustrating a display system according to the present embodiment.
Figure 22:
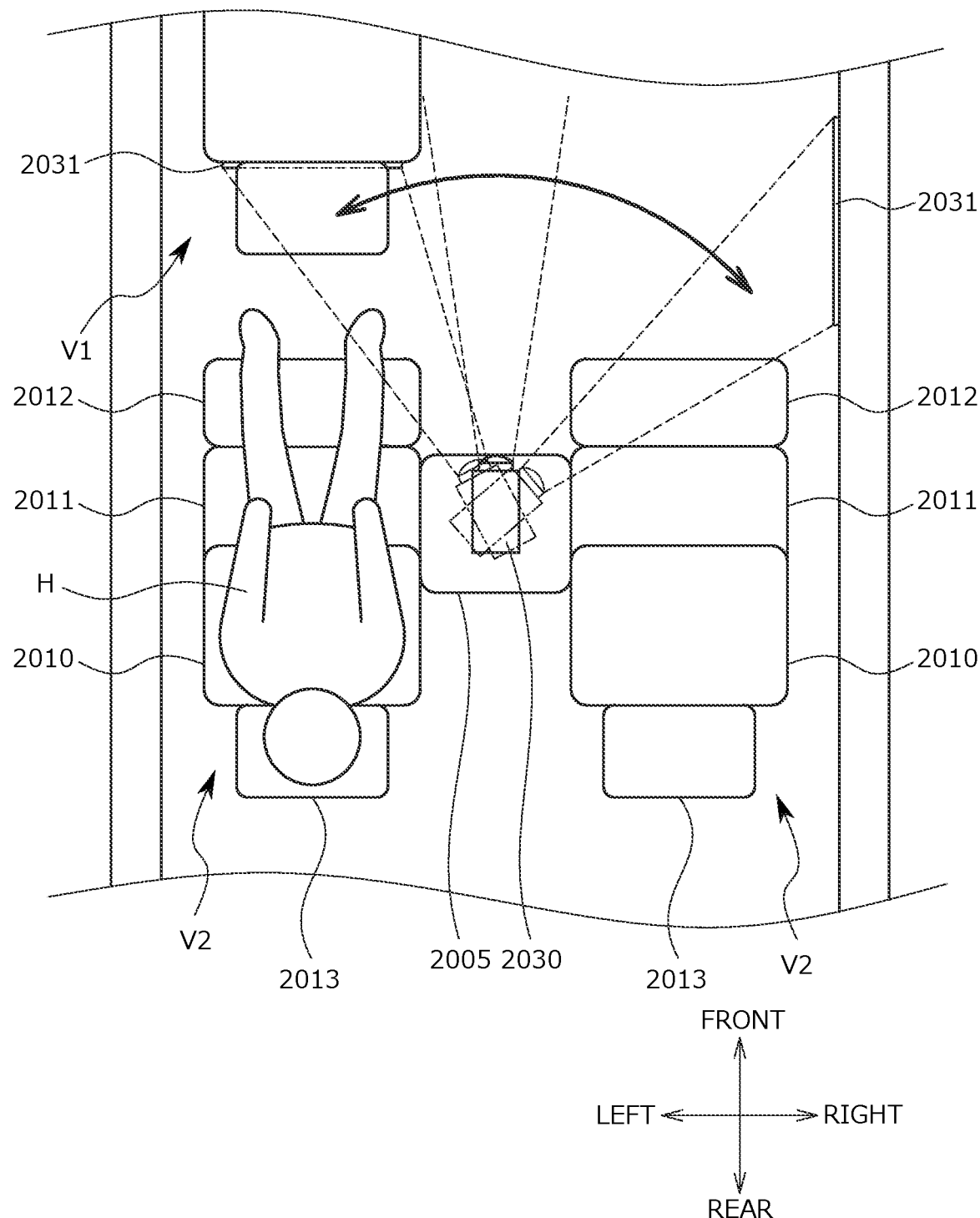
FIG. 22 is a plan view schematically illustrating the display system according to the present embodiment.
Figure 23:
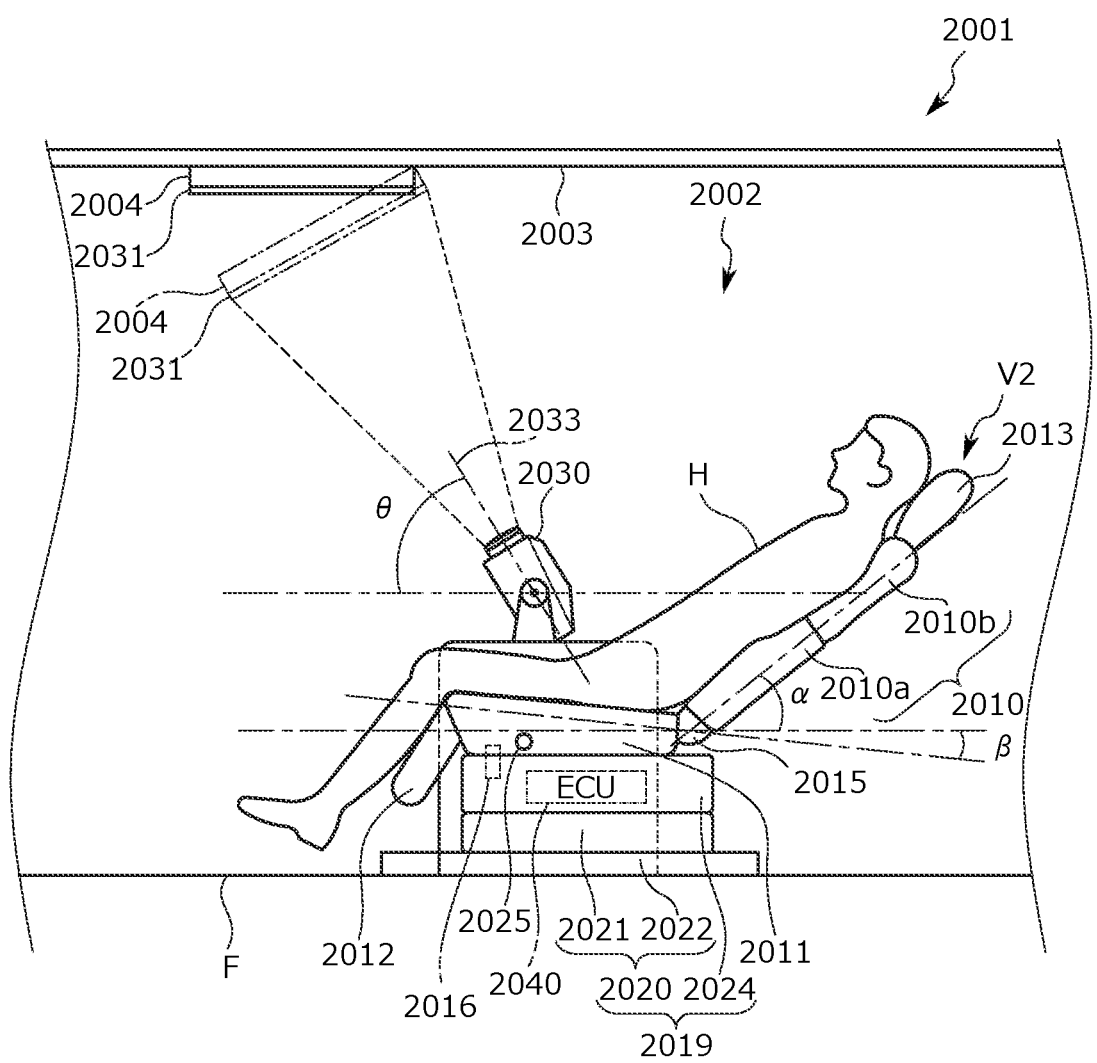
FIG. 23 is a side view illustrating a state where a seat is reclined, in the display system.
Figure 24:
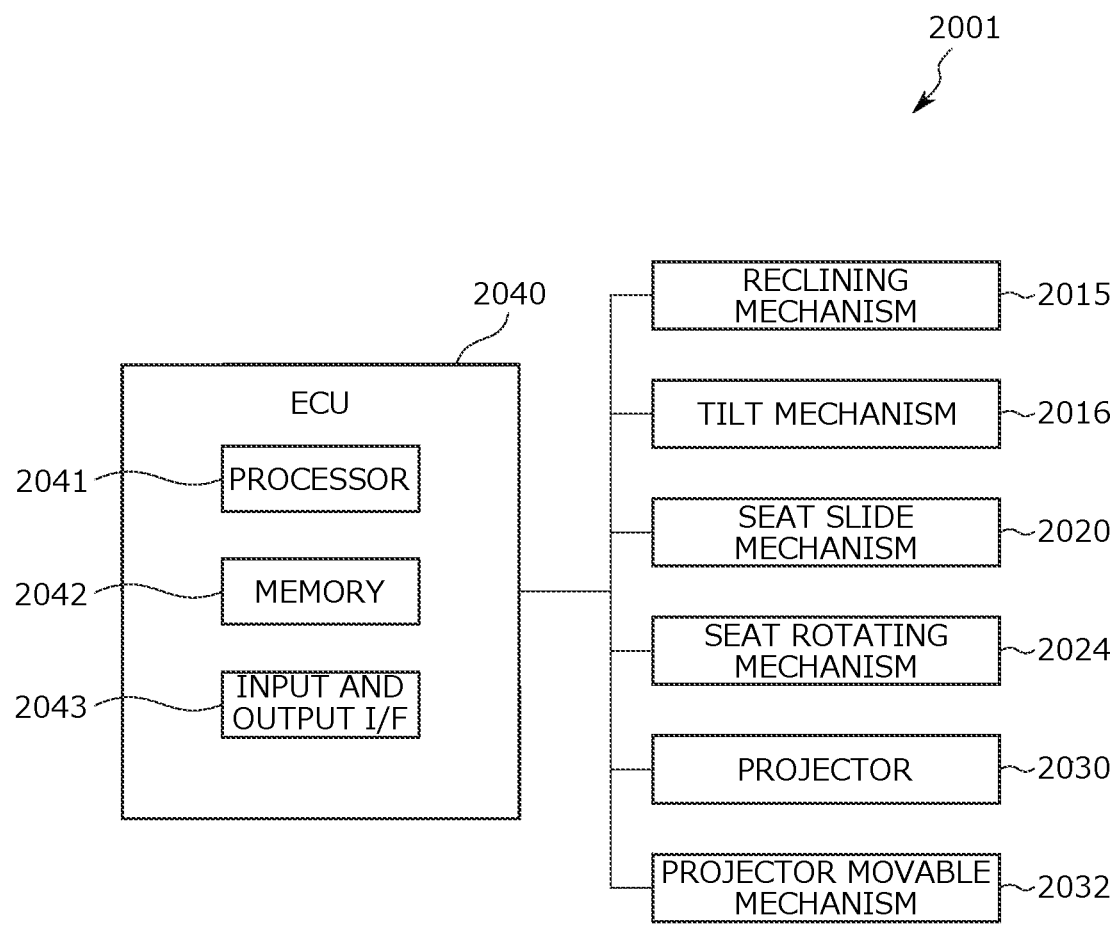
FIG. 24 is a diagram illustrating an ECU and control targets of the ECU.

In the following description, the "front to rear direction" means a front to rear direction when viewed from an occupant (may be called a seated occupant) in a vehicle seat V as illustrated in FIG. 21, and is a direction coinciding with a travel direction of the vehicle. The "seat width direction" means a width direction of the vehicle seat V as illustrated in FIG. 22, and coincides with a right to left direction when viewed from the occupant in the vehicle seat V. In addition, the "up to down direction" means a height direction of the vehicle seat V, and coincides with an up to down direction of the vehicle seat V when viewed from side as illustrated in FIG. 21.

First, the configuration of the vehicle seat V will be described with reference to FIGS. 21 to 24. The vehicle seat V is a seat which is mounted in the vehicle and in which an occupant H can be seated. Hereinafter, a rear seat V2 disposed on a rear side of the vehicle will be mainly described, and a front seat V1 disposed on a front side also has the same configuration.

Then, the vehicle seat V according to the present embodiment can be transformed into at least two states, namely, an upright posture (refer to FIG. 21) in which a seat back portion 2010 is upright and a reclined posture (refer to FIG. 22) in which the seat back portion 2010 is inclined backward. Incidentally, when the vehicle seat V is in the upright posture, the occupant H takes a normal upright posture (for example, driving posture) with respect to the vehicle seat V. On the other hand, when the vehicle seat V is in the reclined posture, the occupant H takes a neutral posture with respect to the vehicle seat V.

As illustrated in FIGS. 21 to 22, a display system 2001 includes the vehicle seat V in which the occupant H is seated; a projector 2030 which projects an image 2031 onto a wall surface inside the vehicle; and an electronic control unit (ECU) 2040 as a control unit that controls operation of each part of the vehicle seat V.

The projector 2030 is attached to a center console 2005 provided beside the vehicle seat V. The projector 2030 can change the direction of a lens by itself to change the position, the angle, or the like of image projection. In addition, the body of the projector 2030 is attached to a projector movable mechanism 2032, and the angle in a vertical direction and the angle in a horizontal direction of the projector 2030 with respect to the vehicle can be changed.

The vehicle seat V includes the seat back portion 2010; a seat cushion portion 2011; an ottoman portion 2012; a headrest portion 2013; and a seat support portion 2019. In addition, a reclining mechanism 2015 which operates the seat back portion 2010 so as to be inclined and a tilt mechanism 2016 which inclines the seat cushion portion 2011 are provided. In addition, the seat support portion 2019 includes a seat slide mechanism 2020 that moves the vehicle seat V in the front to rear direction or in the right to left direction, and a seat rotating mechanism 2024 that rotates the vehicle seat V around an axis along the up to down direction.

The seat back portion 2010 supports the back of the occupant H from rear, and is formed by supporting a cushion material with a frame not illustrated, and covering the cushion material with a skin material.

Incidentally, the seat back portion 2010 according to the present embodiment is divided into two sections in the up to down direction, and includes a seat back upper portion 2010a and a seat back lower portion 2010b. The seat back upper portion 2010a supports a portion of the back of the occupant H, the portion being located at the same height of the chest. The seat back lower portion 2010b supports a portion of the back of the occupant, the portion lying from the abdomen to the lumbar.

In addition, the seat back portion 2010 can be moved (strictly, rotated) to be inclined backward with respect to the seat cushion portion 2011, so to speak, can be reclined by the reclining mechanism 2015.

The reclining mechanism 2015 is a mechanism that moves (rotates) the seat back portion 2010 to change the angle at which the seat back portion 2010 is reclined with respect to the vehicle (recline angle α), and is realized, for example, by driving a motor (not illustrated). When the reclining mechanism 2015 operates, the seat back portion 2010 rotates around a shaft member that connects the seat back portion 2010 and the seat cushion portion 2011. A hall IC is provided in the motor provided in the reclining mechanism 2015, to output a pulse each time the motor makes one rotation. The pulse is received by the ECU 2040, so that the recline angle α of the seat back portion 2010 can be measured.

The seat cushion portion 2011 supports the buttocks of the occupant H from below, and is formed by placing a cushion material on a frame not illustrated, and covering the cushion material with a skin material. A rear end portion of the seat cushion portion 2011 is connected to a lower end portion of the seat back portion 2010 (strictly, a lower end portion of the seat back lower portion 2010b) via a shaft extending along the seat width direction.

In addition, the tilt mechanism 2016 can rotate the seat cushion portion 2011 according to the present embodiment such that a front end portion of the seat cushion portion 2011 is lifted and lowered in the up to down direction.

The tilt mechanism 2016 is a mechanism which moves (rotates) the seat cushion portion 2011 such that the front end portion of the seat cushion portion 2011 is lifted and lowered, and, for example, is formed of a jack type electric lift mechanism. When the tilt mechanism 2016 operates, a front end of the seat cushion portion 2011 rotates with respect to a rear end of the seat cushion portion 2011. A hall IC is provided in a motor which drives the tilt mechanism 2016, to output a pulse each time the motor makes one rotation. The output pulse is received by the ECU 2040, so that the angle at which the seat cushion portion 2011 is inclined with respect to a vehicle body floor F (inclination angle β) can be measured.

The ottoman portion 2012 supports the lower legs of the occupant H from below, and is formed by placing a cushion material on a frame board not illustrated, and covering the cushion material with a skin material. The ottoman portion 2012 is supported on the front end portion of the seat cushion portion 2011 via a rotating shaft extending along the seat width direction. Namely, the ottoman portion 2012 can rotate around the rotating shaft.

Then, the ottoman portion 2012 rotates to move between a deployment position and a storage position. The storage position is a position when the ottoman portion 2012 is not used, and is a position when the ottoman portion 2012 hands down and a tip portion (free end portion) of the ottoman portion 2012 is closest to the seat cushion portion 2011. The deployment position is a position at which the ottoman portion 2012 is used (to put it simply, a position at which the lower legs of the occupant can be supported), and is a position when the ottoman portion 2012 extends forward from the front end of the seat cushion portion 2011.

In addition, the length (hereinafter, entire length) of the ottoman portion 2012 from a base end portion supported on the seat cushion portion 2011 to the tip portion which is the free end portion can be extended and contracted. Namely, the ottoman portion 2012 is configured such that the entire length is shortest when the ottoman portion 2012 is at the storage position, and the entire length is gradually increased as the ottoman portion 2012 approaches the deployment position.

In addition, in the present embodiment, the headrest portion 2013 can be moved upward and downward with respect to the seat back portion 2010 by a headrest moving mechanism (not illustrated). Namely, in the present embodiment, the position at which the head of the occupant is supported can be changed according to movement of the headrest portion 2013 by the headrest moving mechanism.

The seat support portion 2019 is a device that supports the vehicle seat V from below, and is attached to a lower portion of the seat cushion portion 2011. Specifically, the seat support portion 2019 is formed by covering a frame member, which connects the vehicle seat V to the seat slide mechanism 2020 and the seat rotating mechanism 2024, with a cover member. Incidentally, the ECU 2040 is accommodated inside the seat support portion 2019, as a control unit that controls each part of the vehicle seat V. Naturally, the ECU 2040 is not limited to being accommodated inside the seat support portion 2019, and may be accommodated inside the seat back portion 2010, the seat cushion portion 2011, or the like, or may be externally attached to the vehicle seat V.

The seat slide mechanism 2020 is a mechanism that slides the vehicle seat V with respect to the vehicle body floor F in the front to rear direction and in the right to left direction. The seat slide mechanism 2020 includes an upper rail 2021; a lower rail 2022; and a slide motor that slides the upper rail 2021 with respect to the lower rail 2022. A hall IC is also attached to the slide motor to output a pulse each time the motor makes one rotation.

The upper rail 2021 is fixed to the vehicle seat V via the seat support portion 2019, and the lower rail 2022 is fixed to the vehicle body floor F. Here, when the slide motor operates to slide the upper rail 2021 forward and rearward or rightward and leftward with respect to the lower rail 2022, the vehicle seat V, namely, the seat back portion 2010, the seat cushion portion 2011, the headrest portion 2013, and the ottoman portion 2012 can be integrally moved forward and rearward or rightward and leftward with respect to the vehicle body floor F.

The seat rotating mechanism 2024 is a mechanism that rotates the vehicle seat V around the axis along the up to down direction with respect to the vehicle body floor F. The seat rotating mechanism 2024 includes a seat rotating motor. A hall IC is also attached to the seat rotating motor to output a pulse each time the motor makes one rotation. The pulse is received by the ECU 2040, thereby the rotation angle of the vehicle seat V with respect to a movement direction of the vehicle can be measured.

In addition, the vehicle seat V includes an operation switch 2025. The operation switch 2025 is an operation unit that is provided in a side portion of the seat cushion portion 2011 of the vehicle seat V to instruct the vehicle seat V to be transformed in posture. For example, the operation switch 2025 may include a first switch that causes the vehicle seat V to be transformed from the upright posture to the reclined posture, and a second switch that causes the vehicle seat V to be transformed from the reclined posture to the upright posture.

The ECU 2040 is a control unit that controls the reclining mechanism 2015, the tilt mechanism 2016, the seat slide mechanism 2020, the seat rotating mechanism 2024, the projector 2030, and the projector movable mechanism 2032 which have been described above. In addition, the ECU 2040 receives pulses from the motors that are provided in the reclining mechanism 2015, the tilt mechanism 2016, the seat slide mechanism 2020, the seat rotating mechanism 2024, and the projector movable mechanism 2032 (hereinafter, may be collectively called a movable mechanism). Then, as illustrated in FIG. 223, the ECU 2040 includes a processor 2041; a memory 2042; and an input and output interface 2043.

The processor 2041 is a central processing unit that executes various arithmetic processes based on a program or data stored in the memory 2042 and a signal received from each device connected via the input and output interface 2043, and controls each part of the display system 2001. The memory 2042 is, for example, a semiconductor memory, and also functions as a working memory of the processor 2041 in addition to storing various programs or data. The input and output interface 2043 is connected to the reclining mechanism 2015, the tilt mechanism 2016, the seat slide mechanism 2020, the seat rotating mechanism 2024, the projector 2030, the projector movable mechanism 2032, and the operation switch 2025 to communicate with each device.

In addition, as described above, the vehicle seat V is provided with the operation switch 2025 for switching the posture. The operation switch 2025 is a push button type switch provided in a door or an armrest of the vehicle, and is operated when the occupant seated in the vehicle seat V switches the posture of the seat back portion 2010 or the like.

Incidentally, in the present embodiment, the operation switch 2025 is turned on and off to switch the posture of the vehicle seat V; however, while the operation switch 2025 is pressed down, the reclining mechanism 2015 may operate such that the seat back portion 2010 is gradually inclined to suit the preference of the occupant H.

In addition, a projection start switch 2034 is provided. When the projection start switch 2034 is pressed, the projector 2030 starts projecting an image. At this time, the ECU 2040 determines the state of the vehicle seat V, for example, whether the vehicle seat V is in the reclined posture or in the upright posture. Specifically, the ECU 2040 acquires the recline angle $\alpha$ of the seat back portion 2010, the inclination angle $\beta$ of the seat cushion portion, and a height h of the seat cushion portion 2011 based on information regarding the rotation speed of the motor of each movable mechanism, and calculates a projection angle $\theta$ at which the projector 2030 projects an image (angle $\theta$ between the vehicle body floor F and a projection axis 2033) from the information.

At this time, the projection angle $\theta$ of the projector 2030 is set based on a corresponding table in which the recline angle $\alpha$ and the optimal projection angle $\theta$ of the projector which corresponds to the recline angle $\alpha$ are stored as illustrated in, for example, Table 1. For example, when the recline angle is 75°, the projection angle $\theta$ of the projector is set to 15°.

Incidentally, basically, the projection angle $\theta$ is set such that an image is located in front of the line of sight of the occupant H when the occupant H is seated. For this reason, for example, in the case of the upright posture as illustrated in FIG. 21, an image may be projected onto the front seat V1 located on the front, and in the case of the reclined posture as illustrated in FIG. 22, an image may be projected onto a screen 2004 provided on a roof 2003.

The ECU 2040 causes the projector 2030 or the projector movable mechanism 2032 to be operated based on the value of the set projection angle $\theta$, to set the projector at an optimal projection angle and to determine the display position of the image 2031.

TABLE 1

| Recline angle $\alpha$ (°) | Projection angle $\theta$ (°) of projector |
|---|---|
| 90 | 0 |
| 85 | 5 |
| 80 | 10 |
| 75 | 15 |
| 70 | 20 |
| 65 | 25 |
| 60 | 30 |
| 55 | 35 |
| 50 | 40 |
| 45 | 45 |
| 40 | 50 |
| 35 | 55 |
| 30 | 60 |

Incidentally, in the above example, the projection angle $\theta$ is obtained based on the corresponding table between the recline angle $\alpha$ and the projection angle $\theta$; however, a corresponding table including the inclination angle $\beta$ of the seat cushion portion 2011 and the height h of the seat cushion may be determined in advance, and the projection angle $\theta$ of the projector 2030 may be calculated based thereon. In addition, the projection angle $\theta$ may be calculated based on the position and the rotation angle of the entirety of the vehicle seat V, and the display position of an image may be determined. In that case, the entirety of the projector 2030 may rotate not only in the up to down direction but also in the right to left direction.

Figure 25:
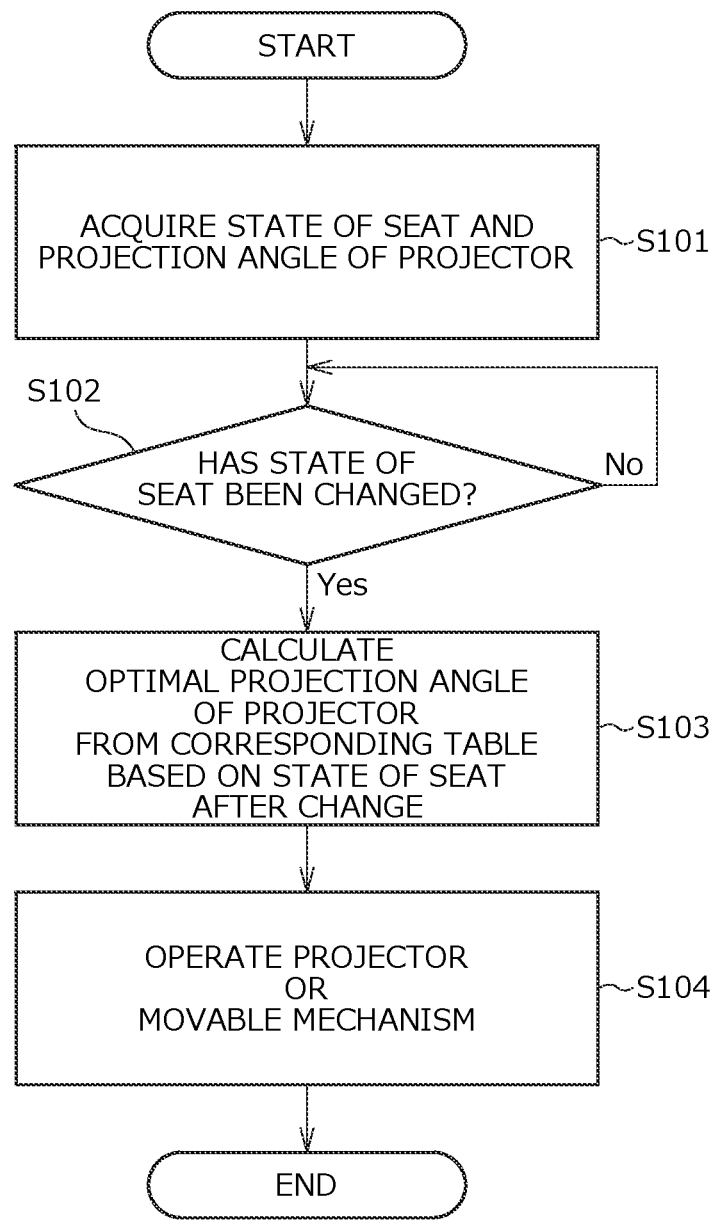
FIG. 25 is a flowchart illustrating control of a projector that operates in connection with operation of the seat.

Hereinafter, a process performed by the display system 2001 from when the projection start switch 2034 is pressed until the display position of the image 2031 projected by the projector 2030 is determined will be described with reference to FIG. 25.

First, when the occupant H presses the projection start switch 2034, the ECU 2040 starts a process of image projection by the projector 2030. Then, the state of the vehicle seat V to which operation of the projector 2030 is adapted, and the state of the projection angle $\theta$ of the projector 2030 are acquired (S101).

Next, it is determined whether or not the state of the vehicle seat V is changed from a state when projection by the projector 2030 has ended previous time (S102). When the state of the vehicle seat V has not been changed, for example, when the state of the vehicle seat V has not been changed from the previous upright state and is in an upright state this time as well (the case of No), a process of changing the projection angle $\theta$ of the projector 2030 ends without need to change the projection angle $\theta$ of the projector 2030.

When in step 102, the ECU 2040 determines that the state of the vehicle seat V has been changed (Yes in step 102), the ECU 2040 obtains the optimal projection angle $\theta$ of the projector 2030 based on the state of the vehicle seat V after change, for example, the recline angle $\alpha$ using the corresponding table stored in the memory 2042 (S103).

Next, the ECU 2040 causes the projector 2030 to be operated or moved using the projector 2030 or the projector movable mechanism. 2032, so that the projection angle $\theta$ of the projector 2030 is the angle obtained in step 103 (S104).

The ECU 2040 can be used in such a manner to set the projection angle θ of the projector 2030 according to the state of the vehicle seat V, and the display position of the image 2031 is determined.

Figure 26:
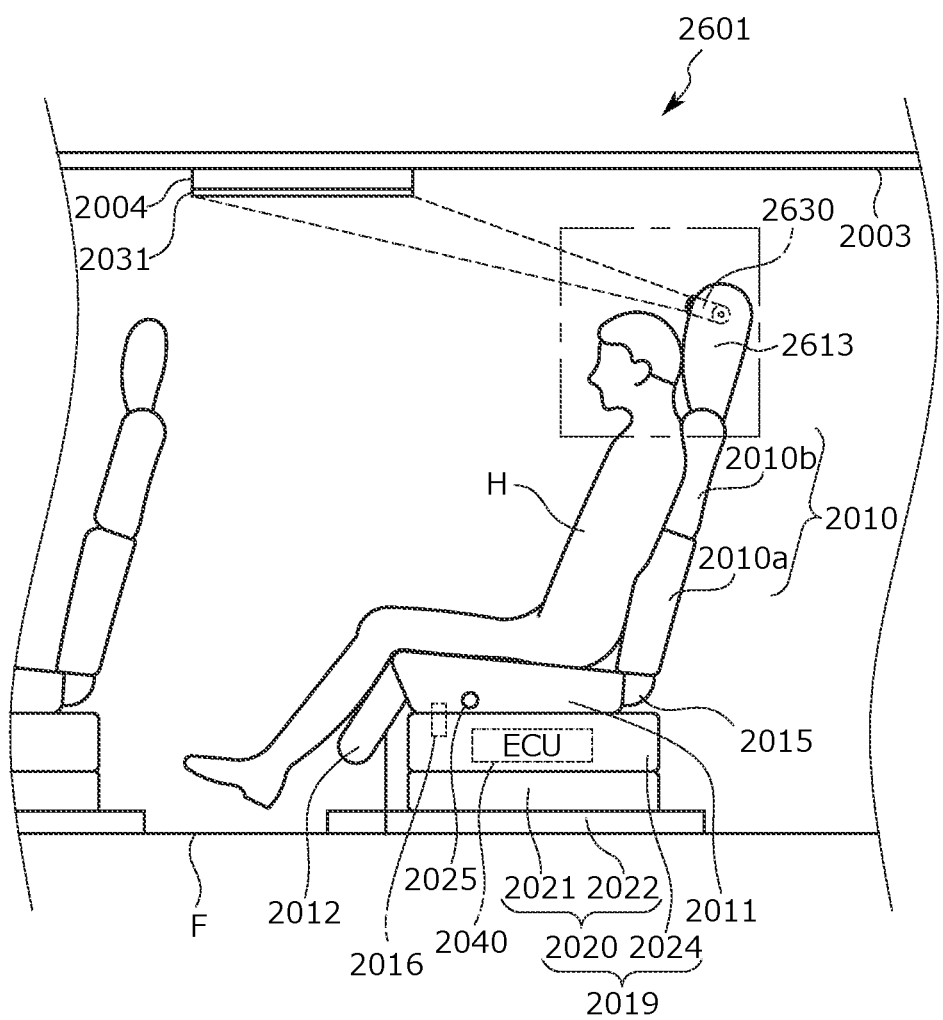
FIG. 26 is a side view illustrating another example of a display system, and is a view illustrating when a projection device is attached to a headrest.
Figure 27:
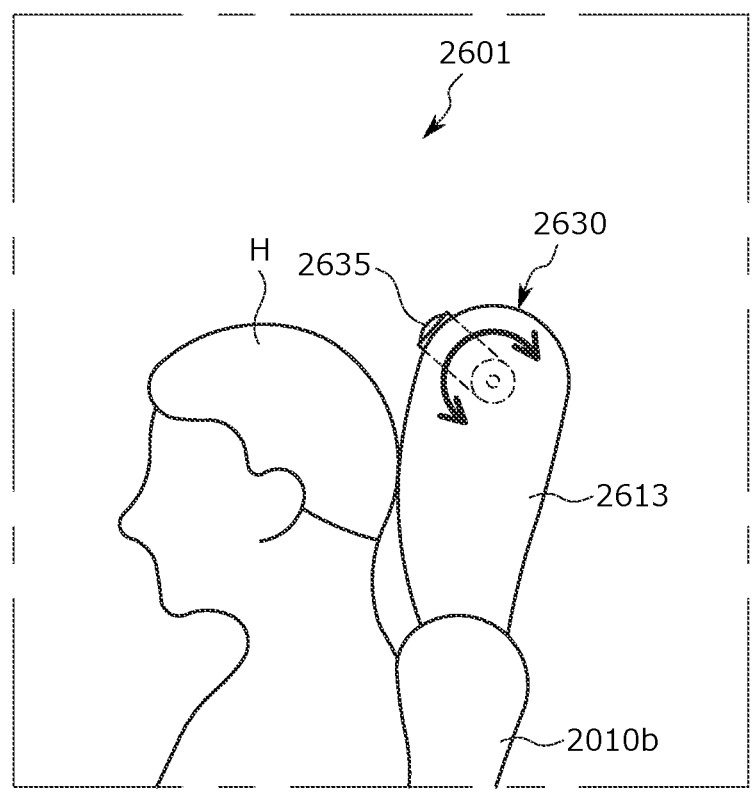
FIG. 27 is a view illustrating the headrest in an enlarged manner illustrated in FIG. 26.

Next, a display system 2601 which is another example will be described with reference to FIGS. 26 and 27. In the display system 2001 illustrated in FIGS. 21 to 23, the projector 2030 is disposed in the center console 2005; however, in the display system 2601 illustrated in FIG. 26, a projector 2630 is mounted in a headrest portion 2613 of a seat in which the occupant H is seated. As illustrated in FIG. 27, a projection unit 2635 of the projector 2630 rotates around an axis along a width direction to change the projection angle θ. The projector 2630 is provided in the headrest portion 2613 to display an image on the roof inside the vehicle. Since configurations other than the structure of the projector 2630 are the same as those of the display system 2001 illustrated in FIG. 21, a detailed description thereof will be omitted.

Figure 28:
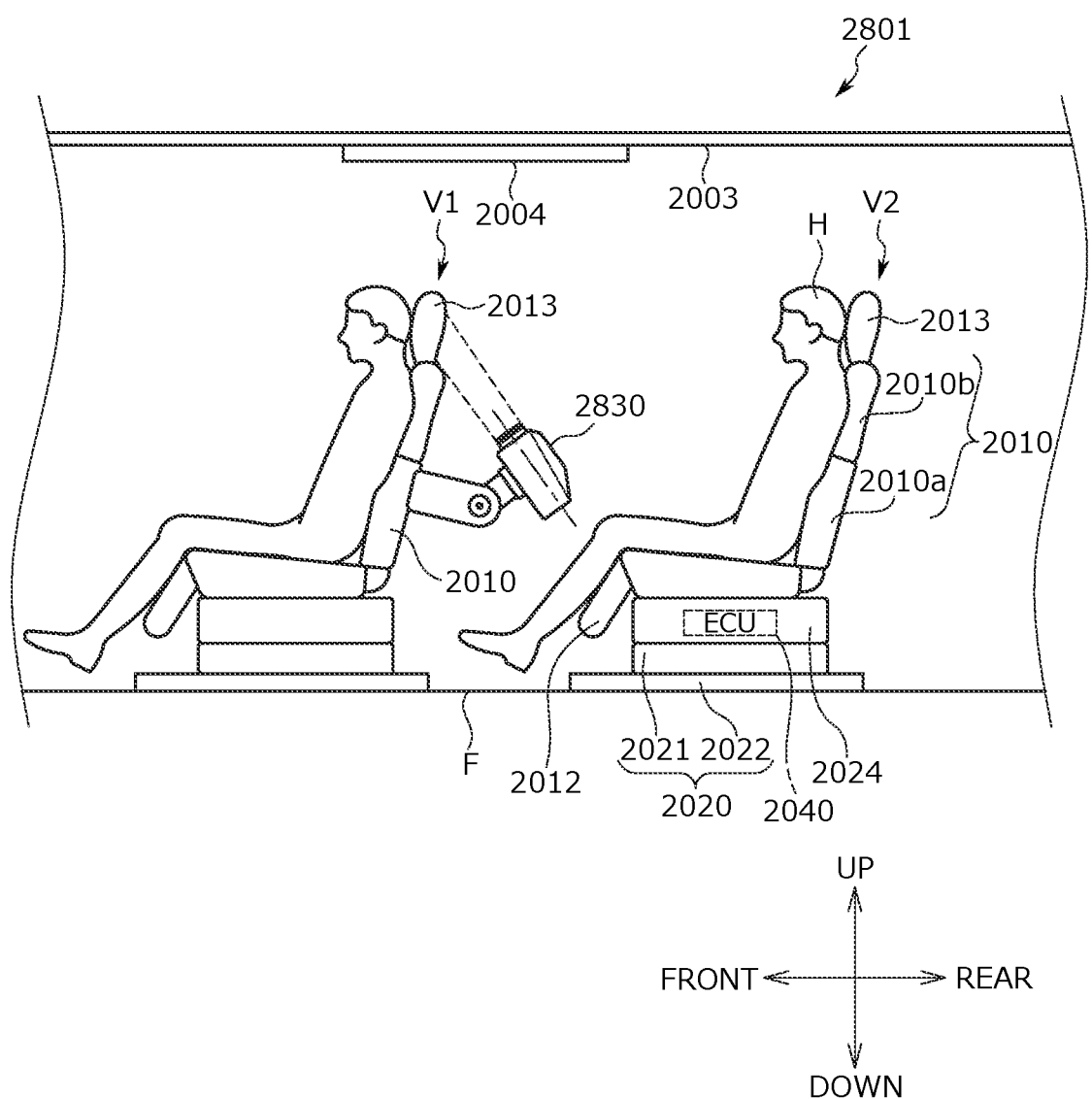
FIG. 28 is a side view illustrating another example of a display system, and is a view illustrating when a projector is attached to a front seat.

Next, a display system 2801 which is another example will be described with reference to FIG. 28. In the display system 2001 illustrated in FIGS. 21 to 23, the projector 2030 is disposed in the center console 2005; however, in the display system 2801 illustrated in FIG. 28, a projector 2830 is provided in the seat back portion 2010 of the front seat V1 installed in front of the rear seat V2 in which the occupant H is seated. When the rear seat V2 is in the upright posture, the projector 2830 installed in the seat back portion 2010 of the front seat V1 may project an image onto the headrest portion 2013 of the front seat V1. When the vehicle seat V is in the reclined posture, the projector 2830 may project a projection image onto the screen 2004 provided on the roof 2003.

In the display system 2001 illustrated in the present embodiment, a projection image is projected onto a back surface of the seat back of the front seat V1 or the roof; however, the position of image projection is not limited thereto, and may be a window or a door.

In addition, the projector 2030 is provided in the center console 2005, the headrest portion 2013, or the seat back portion 2010; however, the installation location of the projector 2030 is not limited thereto, and the projector 2030 may be installed in the armrest of the vehicle seat V.

A plurality of the projectors may be disposed inside the vehicle, and the ECU 2040 may set a vehicle seat that follows each projector.

In the above embodiment, a display system according to the present invention may include a seat which is provided inside a vehicle and of which at least a part is configured to be movable; a projection device which is provided inside the vehicle to able to project an image onto a wall surface inside the vehicle; and a control unit which acquires a state of the seat and controls a projection position of the projection device. The control unit may change the projection position of the projection device according to the state of the seat.

In the display system of the present invention, the projection device which can project an image onto the wall surface inside the vehicle is used as an image display device. In addition, the control unit acquires the state of the seat, and changes the projection position of the projection device, namely, the display position of an image according to the state. For this reason, it is possible to provide the display system in which for example, a large-scale device which supports a display is not provided inside the vehicle, and the state of the seat and the display position of an image are linked to each other.

In this case, the seat may include a seat back portion, a seat cushion portion connected to the seat back portion, and a headrest portion attached to the seat back portion. The control unit may acquire a recline angle of the seat back portion, an inclination angle of the seat cushion portion, and a height of the seat cushion portion from a vehicle body floor to change the projection position of the projection device based on the recline angle, the inclination angle, and the height.

With the above configuration, the projection position of the projection device can be changed to a position optimal for an occupant according to transformation of the seat.

The seat may be such that an entirety of the seat is configured to move or rotationally move in a front to rear direction or in a right to left direction inside the vehicle. The control unit may acquire a position and a rotation angle of the entirety of the seat with respect to the vehicle to change the projection position of the projection device based on the position and the rotation angle of the entirety of the seat.

With the above configuration, the projection position of the projection device can be changed to a position optimal for an occupant according to the position of the seat inside the vehicle.

The projection device may be configured such that an angle in a vertical direction and an angle in a horizontal direction of the projection device with respect to the vehicle are changeable. The control unit may change the angles in the vertical direction and in the horizontal direction of the projection device according to the state of the seat.

Since the projection device is movable, the projection position of the projection device can be changed to a position optimal for an occupant.

The projection device may be provided in the seat. Since the projection device is provided in the seat, the projection device can set the projection position according to movement of the seat.

The seat may include a seat back portion, a seat cushion portion connected to the seat back portion, and a headrest portion attached to the seat back portion. The projection device may be provided in the headrest portion.

Since the projection device is provided in the headrest portion, an image is easily projected onto a roof inside the vehicle.

A center console disposed beside the seat may be provided, and the projection device may be provided in the center console.

Since the projection device is disposed at substantially the center of the vehicle, an image can be projected over a wide range inside the vehicle.

A plurality of the seats may be provided inside the vehicle, and the control unit may be configured to randomly set a seat to which operation of the projection device is adapted, among the plurality of seats.

With the above configuration, an image can be projected to a position optimal for a person who needs to follow, for example, an occupant who sees the image.

The wall surface inside the vehicle, onto which the projection device projects the image, may be configured to be movable according to movement of at least a part of the seat.

Since the wall surface onto which an image is projected is moved, the image can be displayed at an easy-to-see angle for an occupant.

The display system may be provided to the vehicle. Since the display system is provided in the vehicle, it is possible to provide an image to an occupant without providing a large-scale device that supports a display device.

In the above embodiment, the display system used in automobiles has been described as a specific example; however, the present invention is not particularly limited thereto, and the display system of this application can be provided in trains, buses, and the like, and can be also used in airplanes, ships, and the like.

In the present embodiment, the display system according to the present invention has been mainly described. Meanwhile, the above embodiment is merely one example for facilitating the understanding of the present invention, and does not limit the present invention. The present invention can be changed or improved without departing from the concept of the present invention, and needless to say, the present invention includes equivalents thereof. Particularly, the shape, the disposition, or the configuration of the through-holes described in the above embodiment are merely one example, and do not limit the present invention.

REFERENCE SIGNS LIST

S, S2, S3, S4, S5, S6, S7, S8, S9, S10, S11: SEAT EQUIPPED WITH SENSOR UNIT
1, 101, 201, 301, 401, 501, 601, 701, 901, 1001: SEAT CUSHION
2, 402, 502, 602, 802: SEAT BACK
3, 503, 803: HEADREST
503a, 803a: PILLAR
4: ARMREST (ATTACHED PORTION)
10, 110, 210, 310, 610: CUSHION PAD
11, 12: SKIN PULL-IN GROOVE
13, 113: CUSHION RECESSED PORTION
20, 620: SKIN MATERIAL
620a: ZIP FASTENER
21, 22, 23, 24: SKIN POCKET (ATTACHED PORTION)
21a, 22a, 23a, 24a: POCKET OPENING
30 (30A, 30B), 130, 230, 330, 430, 530, 630, 730, 830, 930, 1030: SENSOR UNIT
31, 131, 231, 331, 431, 531, 631, 731, 831: SENSOR MODULE
31a, 331a, 431a, 531a: BIOLOGICAL SENSOR
31b, 331b, 431b: WIRELESS COMMUNICATION UNIT, WIRED COMMUNICATION UNIT (COMMUNICATION UNIT)
31c: CONTROL UNIT
31d: BATTERY UNIT
32, 132, 232, 332, 432, 532, 632, 732, 832: SENSOR HOLDER
32a, 432a: CUSHION MATERIAL
32b: CLOTH MEMBER
32c, 432c: COVER MATERIAL
32d, 432d: COVER CLOSING PORTION
32e, 432e: POSITIONING DISPLAY PORTION
32f (32Af, 32Bf), 432f: SEAT ATTACHMENT PORTION (ATTACHMENT PORTION)
133, 433: STORAGE RECESSED PORTION
434: SLIT HOLE
533, 633, 733, 833: SEAT ATTACHMENT PORTION (ATTACHMENT PORTION)
533a: UPPER COVER (REAR COVER)
533b: LOWER COVER (FRONT COVER)
633a: ZIP FASTENER
733a: LEFT COVER
733b: RIGHT COVER
833a: INSERTION HOLE
833b: HOOK HOLE
534: INSERTION HOLE
535: ENGAGING HOOK
536: ENGAGEMENT MEMBER
734: PROTECTIVE COVER
834: HOOK
835: TABLE
340: ECU
S12: SHOE EQUIPPED WITH SENSOR UNIT
1101: INSOLE
1101a: STORAGE RECESSED PORTION
1130: SENSOR UNIT
2001, 2601, 2801: VEHICLE DISPLAY SYSTEM (DISPLAY SYSTEM)
2002: INSIDE VEHICLE
2003: ROOF
2004: SCREEN
2005: CENTER CONSOLE
2010: SEAT BACK PORTION
2010a: SEAT BACK UPPER PORTION
2010b: SEAT BACK LOWER PORTION
2011: SEAT CUSHION PORTION
2012: OTTOMAN PORTION
2013, 2613: HEADREST PORTION
2015: RECLINING MECHANISM
2016: TILT MECHANISM
2019: SEAT SUPPORT PORTION
2020: SEAT SLIDE MECHANISM
2021: UPPER RAIL
2022: LOWER RAIL
2024: SEAT ROTATING MECHANISM
2025: OPERATION SWITCH
2030, 2630, 2830: PROJECTOR (PROJECTION DEVICE)
2031: PROJECTION IMAGE
2032: PROJECTOR MOVABLE MECHANISM
2033: PROJECTION AXIS OF PROJECTOR
2034: PROJECTION START SWITCH
2635: PROJECTION UNIT
2040: ECU
2041: PROCESSOR (CONTROL UNIT)
2042: MEMORY (STORAGE UNIT)
2043: INPUT AND OUTPUT INTERFACE
F: VEHICLE BODY FLOOR
V: VEHICLE SEAT
V1: FRONT SEAT
V2: REAR SEAT
α: RECLINE ANGLE
β: INCLINATION ANGLE
θ: PROJECTION ANGLE
H: OCCUPANT

The invention claimed is:

1. A sensor unit that is attached to a seat in which a seated occupant is seated, the sensor unit comprising:
a biological sensor that detects a biological signal of the seated occupant;
a communication unit that is connected to the biological sensor to transmit the detected biological signal to an outside; and
a sensor holder that holds the biological sensor and the communication unit,
wherein the sensor holder includes a seat attachment portion detachably attached to an attached portion that is provided in the seat at a position at which the seated occupant is abuttable against the attached portion,
the seat attachment portion is provided in both end portions in a longitudinal direction of the sensor holder, and
the seat attachment portion is attached to the attached portion of the seat such that a front surface, an upper surface, a bottom surface, and a rear surface of the attached portion are covered with the seat attachment portion.

2. The sensor unit according to claim 1, further comprising:
a wireless communication unit as the communication unit that wirelessly transmits the detected biological signal to the outside; and
a battery unit that is connected to the biological sensor and the wireless communication unit to supply electric power.

3. The sensor unit according to claim 1,
wherein the sensor holder holds a plurality of the biological sensors, and
the plurality of biological sensors are disposed at intervals in a seat width direction and/or in a seat front to rear direction, and are disposed to correspond to positions at which the seated occupant is abuttable against the plurality of biological sensors.

4. The sensor unit according to claim 1,
wherein a positioning display portion which displays a holding position of the biological sensor to the outside is formed in a front surface of the sensor holder.

5. A seat equipped with a sensor unit comprising:
the sensor unit according to claim 1; and
a seat cushion formed by covering a cushion pad with a skin material,
wherein the sensor unit is detachably attached on the seat cushion.

6. The sensor unit according to claim 1,
wherein the seat attachment portion includes an upper cover that is attached to an upper end portion of the sensor holder, and a lower cover that is attached to a lower end portion of the sensor holder,
an engagement member is fixed to an extending end portion of the upper cover,
an engaged member is fixed to an extending end portion of the lower cover,
the seat attachment portion is attached to a seat back provided as the attached portion by engaging the engagement member to the engaged member, and the upper cover and the lower cover cover the front surface, the upper surface, the bottom surface, and the rear surface of the seat back.

7. The sensor unit according to claim 1,
wherein the seat attachment portion includes a rear cover that is attached to a rear end portion of the sensor holder, and a front cover that is attached to a front end portion of the sensor holder,
an engagement member is fixed to an extending end portion of the rear cover,
an engaged member is fixed to an extending end portion of the front cover,
the seat attachment portion is attached to a seat cushion provided as the attached portion by engaging the engagement member to the engaged member, and
the rear cover and the front cover cover the front surface, the upper surface, the bottom surface, and the rear surface of the seat cushion.

8. A method for manufacturing a seat equipped with a sensor unit, wherein the sensor unit has a biological sensor that detects a biological signal of the seated occupant, a communication unit that is connected to the biological sensor to transmit the detected biological signal to an outside and a sensor holder that holds the biological sensor and the communication unit, the method comprising:
preparing the seat in which a seated occupant is seated; and
attaching the sensor unit to the seat,
wherein the sensor holder includes a seat attachment portion detachably attached to an attached portion that is provided in the seat at a position at which the seated occupant is abuttable against the attached portion,
wherein the seat attachment portion is provided in both end portions in a longitudinal direction of the sensor holder, and
wherein the seat attachment portion is attached to the attached portion of the seat such that a front surface, an upper surface, a bottom surface, and a rear surface of the attached portion are covered with the seat attachment portion.

* * * * *